(12) United States Patent
Barrett et al.

(10) Patent No.: US 11,744,698 B2
(45) Date of Patent: *Sep. 5, 2023

(54) EXTENDED DEPTH OF FOCUS INTRAOCULAR LENSES AND ASSOCIATED METHODS

(71) Applicant: Rayner Intraocular Lenses Limited, West Sussex (GB)

(72) Inventors: Graham Barrett, City Beach (AU); Tjundewo Lawu, Tokyo (JP)

(73) Assignee: Rayner Intraocular Lenses Limited, West Sussex (GB)

( * ) Notice: Subject to any disclaimer, the term of this patent is extended or adjusted under 35 U.S.C. 154(b) by 497 days.

This patent is subject to a terminal disclaimer.

(21) Appl. No.: 16/878,690

(22) Filed: May 20, 2020

(65) Prior Publication Data

US 2020/0276012 A1    Sep. 3, 2020

Related U.S. Application Data

(63) Continuation of application No. 15/393,653, filed on Dec. 29, 2016, now Pat. No. 10,702,376, which is a continuation of application No. 14/234,131, filed as application No. PCT/JP2012/004953 on Aug. 3, 2012, now Pat. No. 9,901,441.

(60) Provisional application No. 61/515,311, filed on Aug. 4, 2011.

(51) Int. Cl.
*A61F 2/16* (2006.01)

(52) U.S. Cl.
CPC ............ *A61F 2/1637* (2013.01); *A61F 2/164* (2015.04); *A61F 2/1613* (2013.01); *A61F 2/1621* (2013.01); *A61F 2002/1699* (2015.04)

(58) Field of Classification Search
CPC ....... A61F 2/1621; A61F 2/1637; A61F 1/164
See application file for complete search history.

(56) References Cited

U.S. PATENT DOCUMENTS

| | | | |
|---|---|---|---|
| 2005/0119739 A1* | 6/2005 | Glazier | A61F 2/1613 623/6.37 |
| 2010/0234943 A1* | 9/2010 | Portney | A61F 2/1618 623/6.23 |

* cited by examiner

*Primary Examiner* — Leslie Lopez
(74) *Attorney, Agent, or Firm* — Harris Beach PLLC

(57) ABSTRACT

A method improves depth of focus in a first eye only by adding a higher order aberration (HOA) to the first eye by adding a monofocal optical device to the first eye. The method may also correct a spherical aberration in a second eye by inserting a monofocal aspheric IOL. The HOA added to the first eye may be selected from the group consisting of spherical, trefoil and coma. Additionally, the monofocal optical device inserted into the first eye may comprise a monofocal aspheric IOL that adds spherical aberration to the first eye. The optical device inserted into the first eye may comprise a 20 D monofocal aspheric IOL that adds 0.4 μm of spherical aberration to the first eye at 6 mm entrance pupil and adds 0.1 μm of spherical aberration to the first eye at 4 mm entrance pupil.

13 Claims, 12 Drawing Sheets

IOL Eliminates Aberration

Spherical IOL

Aspheric IOL Adds Aberration

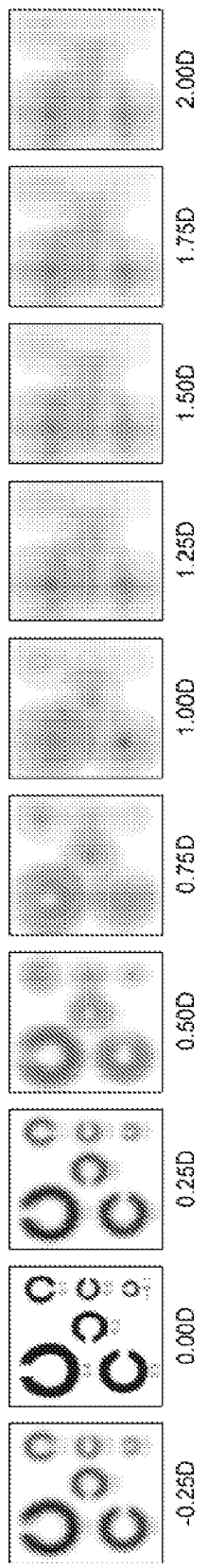
FIG. 3A IOL Eliminates Aberration
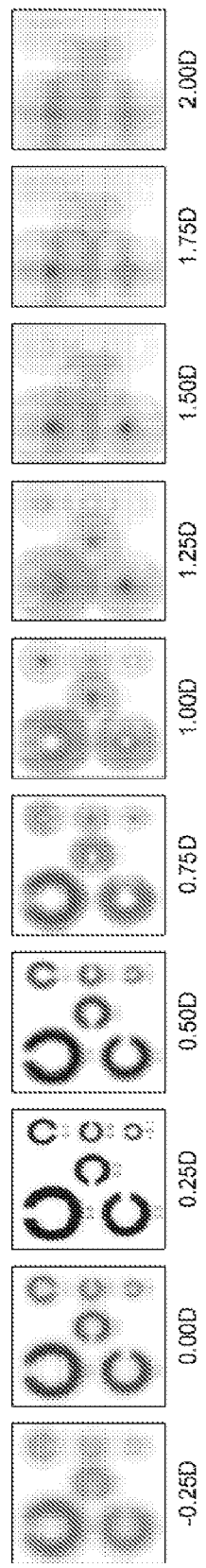
FIG. 3B Spherical IOL
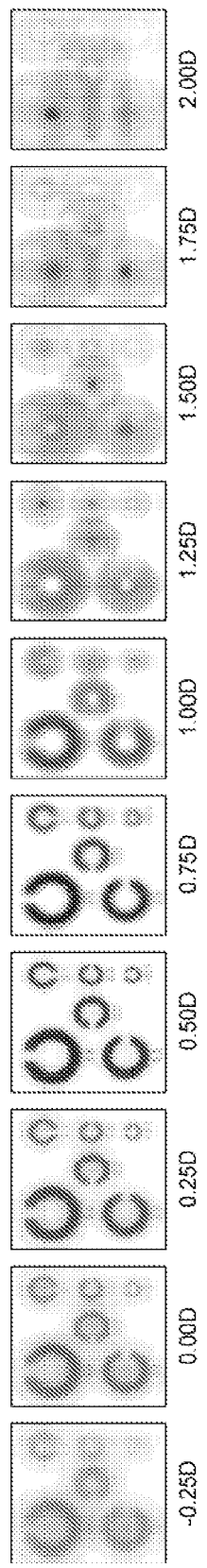
FIG. 3C Aspheric IOL Adds Aberration

EXTENDED DEPTH OF FOCUS INTRAOCULAR LENSES AND ASSOCIATED METHODS

CROSS-REFERENCE TO RELATED APPLICATIONS

This application is a continuation of U.S. application Ser. No. 15/393,653, filed Dec. 29, 2016, which is a continuation of U.S. application Ser. No. 14/234,131, filed Mar. 27, 2014, which is the U.S. National Stage of PCT App. Ser. No. PCT/JP2012/004953, filed Aug. 3, 2012, which claims priority to U.S. Prov. App. Ser. No. 61/515,311, filed Aug. 4, 2011, each of which is incorporated herein by reference.

BACKGROUND OF THE INVENTIONS

Field of the Inventions

The present inventions relate generally to intraocular lenses.

Description of the Related Art

There are many instances where an intraocular lens (IOL) is inserted into eye. For example, the crystalline lens within a person's eye may become clouded due to cataract. The clouded lens may be surgically removed and replaced with an IOL. The IOL may, in addition, be used to provide refractive vision correction.

Pseudophakic monovision is a method of correcting presbyopia by using IOLs to correct the dominant eye for distance vision and the non-dominant eye for near vision in an attempt to achieve spectacle-free binocular vision from far to near. The goal is emmetropia in the dominant eye and myopia (e.g., 1.5 to 2.5 D of defocus) in the nondominant eye, i.e., high contrast distance and near vision. The use of standard monofocal IOLs in pseudophakic monovision procedures can be problematic for a variety of reasons. For example, standard monofocal IOLs do not preserve natural accommodation. Given that the target refraction is emmetropia in the dominant eye and myopia in the non-dominant eye, a large degree of anisometropia is needed to obtain excellent near visual acuity. The result is, however, a loss of near stereopsis, poor intermediate visual acuity, uncomfortable monocular suppression of visual input.

One example of a conventional pseudophakic monovision procedure, where the IOL for the near vision eye has a power that is 2.0 D greater than the IOL power required to achieve emmetropia in the distance eye, is illustrated in FIGS. 1A and 1B. The IOLs are aspheric IOLs that eliminate (or at least substantially eliminate) the spherical aberration of the eye to provide high levels of contrast and visual acuity. It should also be noted that unless otherwise indicated, when the power difference between the eyes is described herein, both eyes have the same biometry (i.e., the same corneal curvature measured by keratometry and the same axial length), and therefore require the same IOL to be implanted in each eye for emmetropia. Also, the 2.0 D difference mentioned above is the diopter power of the IOL, i.e., is in the IOL plane. The resulting difference in the refractive power of the eye, i.e., in the corneal plane, is slightly different. The corneal plane values are presented in FIGS. 1A and 1B (as well as the similar procedural representations described below). For example, and referring to FIGS. 1A and 1B, 2.0 D greater IOL will result in a myopic defocus of about 1.3 D, depending upon the biometry of the eye.

Also, for illustrative purposes only, visual acuity VA of 0.5 (i.e., 20/40 vision) is considered to be the minimum acceptable value. Referring to FIG. 1A, best focus for the distance and near eyes is 0.2 D and 1.5 D, respectively, and the near eye has acceptable visual acuity up to 1.9 D of defocus. Much of the intermediate visual acuity is below 1.0 (i.e., below 20/20 vision), as shown in FIG. 1B. Also, as should be apparent from the FIG. 1B, there could be a loss of stereoacuity if there was more than 2.0 D of defocus in the near eye.

SUMMARY

An intraocular lens in accordance with at least some of the present inventions includes a monofocal aspheric lens body that defines a focal length and is configured to add more spherical aberration to an eye than a spherical IOL with the same focal length. In at least some implementations, the lens body defines an optical center, an outer edge, a first region that extends from the optical center to a radius between the outer edge and the optical center, and a second region located radially outward of the first region, and the second region is configured to reduce the longitudinal higher order aberration that will occur in low light conditions within an optical system defined by the lens body and the eye.

Methods in accordance with some of the present inventions involve adding higher order aberrations (e.g., spherical, trefoil or coma) to an eye with an optical device (e.g., an IOL or contact lens) to improve depth of focus in that eye, or through the use of corneal refractive surgery. For example, in some implementations, an aspheric IOL may be inserted into the eye to add spherical aberrations to the eye, and improve depth of focus in that eye. In at least some instances, the optical device is a monofocal optical device (e.g., a monofocal IOL or monofocal contact lens) that is configured to reduce the longitudinal higher order aberration that will occur in low light conditions within an optical system defined by the lens body and the eye.

A pseudophakic monovision procedure in accordance with at least one of the present inventions includes inserting an aspheric IOL into one eye that eliminates (or at least substantially eliminates) spherical aberration in the eye and is set for distance vision and inserting an aspheric IOL into the other eye that adds spherical aberration to the eye, thereby increasing depth of focus, and is set for near vision (e.g., 2.0 to 2.5 D greater than the distance eye).

A pseudophakic monovision procedure in accordance with at least one of the present inventions includes inserting an aspheric IOL into one eye that eliminates (or at least substantially eliminates) spherical aberration in the eye and is set for distance vision and inserting an aspheric IOL into the other eye that is set for intermediate vision (e.g., 1.0 to 1.5 D greater than the distance eye).

A pseudophakic monovision procedure in accordance with at least one of the present inventions includes inserting an aspheric IOL into one eye that eliminates (or at least substantially eliminates) spherical aberration in the eye and is set for distance vision and inserting an aspheric IOL into the other eye that adds spherical aberration to the eye, thereby increasing depth of focus, and is set for intermediate vision (e.g., 1.0 to 1.5 D greater than the distance eye). In at least some instances, the IOL is a monofocal asheric IOL that is configured to reduce the longitudinal spherical aberration that will occur in low light conditions within an optical system defined by the lens body and the eye.

In some exemplary implementations, IOLs that add other higher order aberrations may be used in place of those that add spherical aberration.

In some exemplary implementations, an achromatic lens (e.g., a hybrid lens with refractive and diffractive elements) may be used to reduce chromatic aberration in the eye set for distance, thereby improving contrast in the eye set for distance.

The present inventions also include an IOL, contact lens or other optical device that has the appropriate characteristics to perform the methods described above.

The present inventions also include a pair of IOLs, contact lenses or other optical devices, i.e., one for each eye, that have the appropriate characteristics to perform the methods described above.

There are a variety of advantages associated with the present methods and apparatus. For example, as compared to conventional pseudophakic monovision, the present methods and apparatus provide improved binocular visual performance by extending the depth of focus in at least one of the eyes.

BRIEF DESCRIPTION OF THE DRAWINGS

Detailed description of preferred embodiments of the inventions will be made with reference to the accompanying drawings.

FIG. 3A is a Landolt C chart for an eye that includes an IOL which eliminates spherical aberration.

FIG. 3B is a Landolt C chart for an eye that includes a spherical IOL.

FIG. 3C is a Landolt C chart for an eye that includes an aspheric IOL which adds spherical aberration to the eye.

DETAILED DESCRIPTION

The following is a detailed description of the best presently known modes of carrying out the inventions. This description is not to be taken in a limiting sense, but is made merely for the purpose of illustrating the general principles of the invention. Although the exemplary implementations are described below in the context of IOLs that add positive spherical aberration to the eye, the present inventions are also applicable IOLs and ocular implants, including those yet to be developed, that introduce negative spherical aberration (beyond that necessary to eliminate the natural spherical aberration of the eye) as well as other higher order aberrations (e.g., trefoil, other foils and coma).

As discussed in greater detail below, the present inventions include a variety of vision correction techniques that add spherical aberrations (or other higher order aberrations) to one or both eyes with an IOL to improve depth of focus in the eye. Such improvement is referred to herein as extended depth of focus and an IOL that adds, for example, more spherical aberration to the eye than a spherical IOL with an equivalent focal length is referred to as an EDF IOL. The present inventions also include such EDF IOLs and the methods of making them.

Figure 2A:
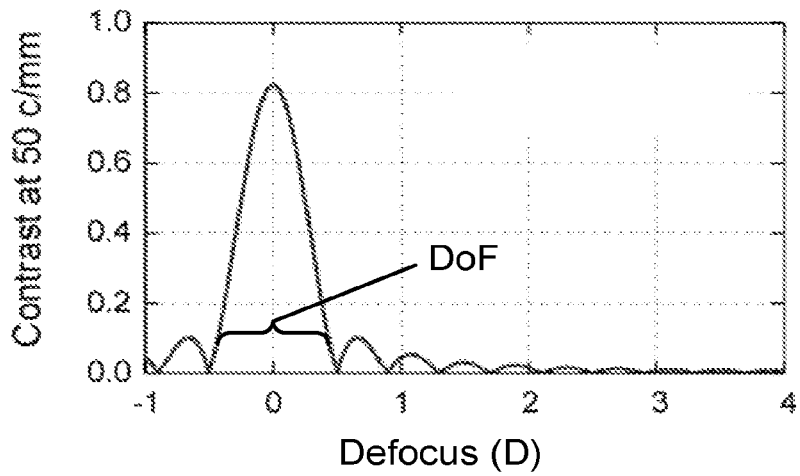
FIG. 2A is a graph showing contrast at 50 cycles per mm as a function of defocus for an eye that includes an IOL which eliminates spherical aberration.
Figure 2B:
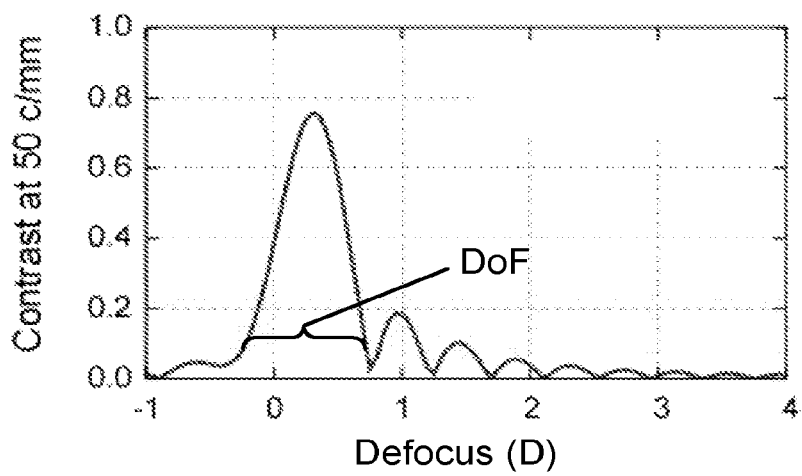
FIG. 2B is a graph showing contrast at 50 cycles per mm as a function of defocus for an eye that includes a spherical IOL.
Figure 2C:
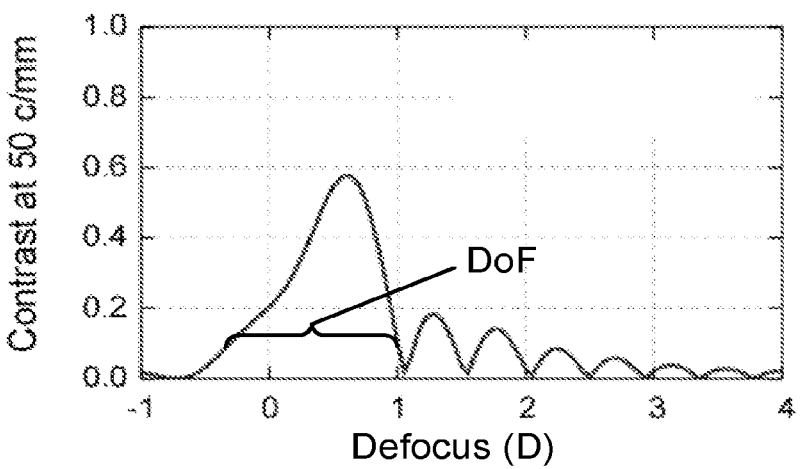
FIG. 2C is a graph showing contrast at 50 cycles per mm as a function of defocus for an eye that includes an aspheric IOL which adds spherical aberration to the eye.

Referring first to FIGS. 2A-2C, which are graphs showing exemplary relationships between contrast (which correlates to visual acuity) and defocus, contrast decreases as depth of focus increases, and depth of focus increases as spherical aberration increases. To that end, a contrast value of 0.1 is considered to render contrast that is sufficient to resolve an image. The use of an aspheric IOL that eliminates the spherical aberration in the eye will result in very high contrast at the paraxial focal point (contrast >0.8 at 0.0 D) and a narrow depth of focus (<≈1.0 D), as is shown in FIG. 2A. The use of a spherical IOL, as shown in FIG. 2B, will result in slightly less contrast at the paraxial focal point (contrast <0.8 at 0.0 D) and a slightly greater depth of focus (≈1.0 D). Turning to FIG. 2C, the use of an aspheric IOL that adds spherical aberration to the eye will result in less contrast at the paraxial focal point (contrast of about 0.2 at 0.0 D and a shift of best contrast to 0.6 at 0.5 D) and a slightly greater depth of focus (≈1.25 D). Similar relationships are illustrated in the Landolt C charts presented in FIGS. 3A-3C.

Figure 4A:
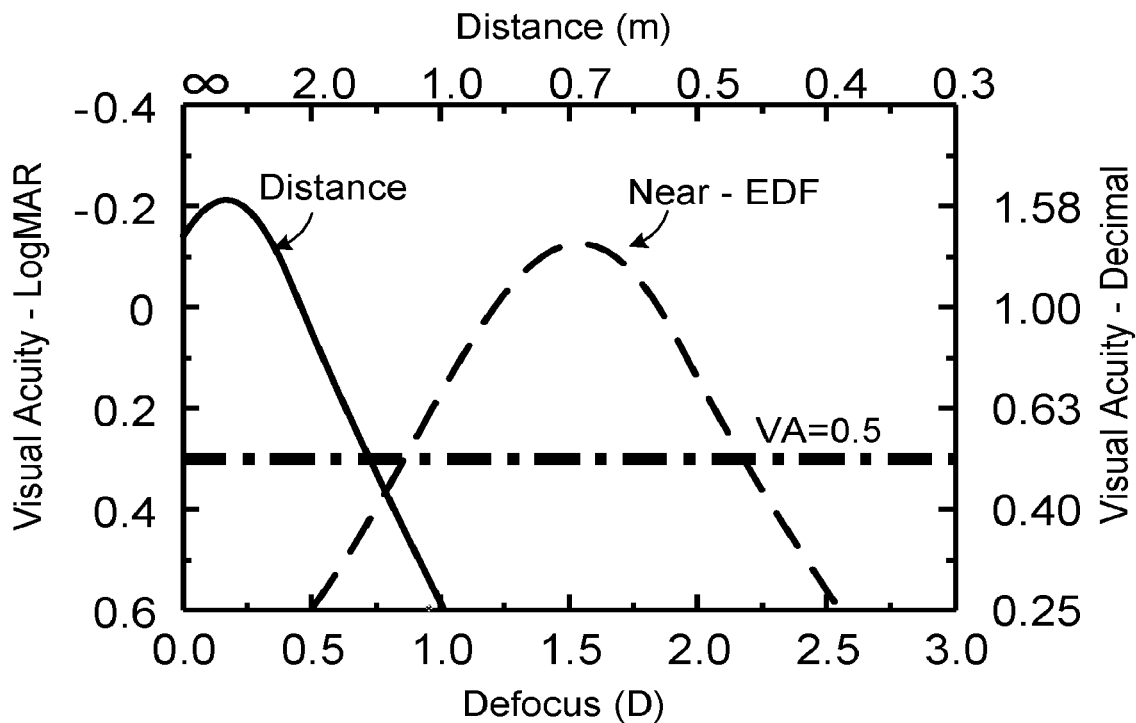
FIG. 4A is a graph showing visual acuity as a function of defocus in each eye after a pseudophakic monovision procedure, in accordance with a present invention, in which the near eye includes an aspheric IOL which adds spherical aberration to the eye.
Figure 4B:
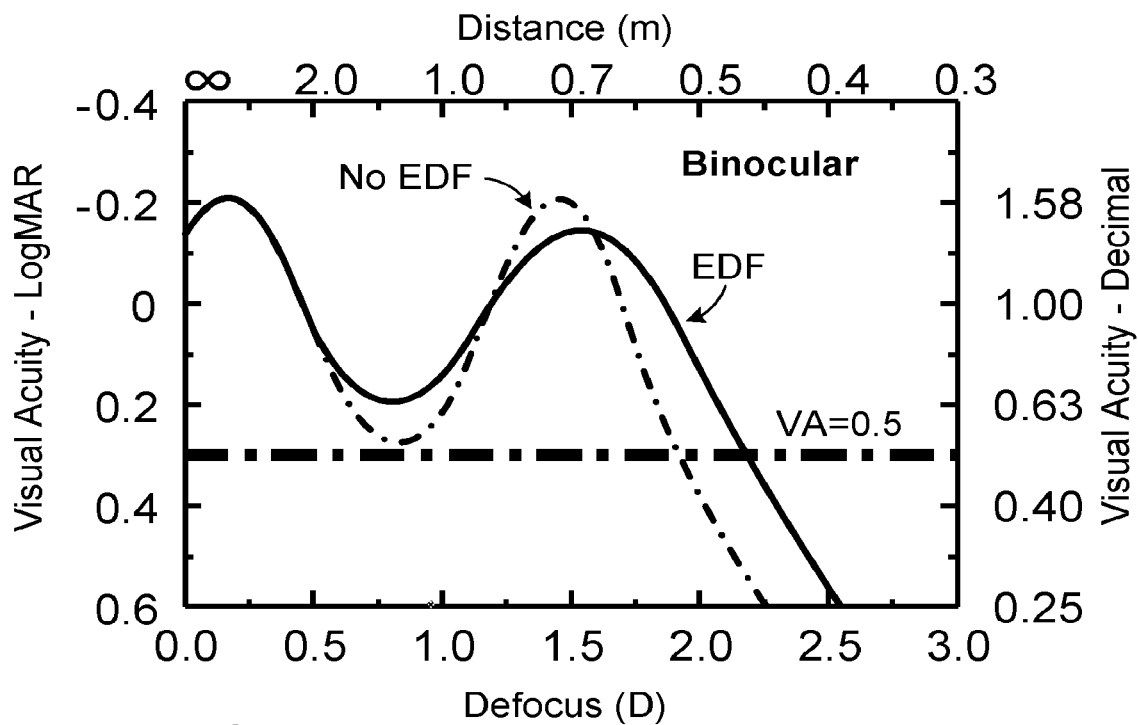
FIG. 4B is a graph showing binocular visual acuity as a function of defocus after the pseudophakic monovision procedure illustrated in FIG. 4A.

Pseudophakic monovision procedures in accordance with at least some of the present inventions include setting the vision in one eye for emmetropia (i.e., the distance eye) and the other eye for myopia (i.e., the near eye). In many instances, and although not necessarily required, the dominant eye will be the distance eye and the non-dominant will be the near eye. Referring to FIG. 4A, in one exemplary procedure, an aspheric IOL that eliminates (or at least substantially eliminates) spherical aberration is inserted into the distance eye. Like the conventional procedure illustrated in FIGS. 1A and 1B, the IOL that is inserted into the near vision eye is 2.0 to 2.5 D greater than the IOL for the distance eye (2.0 D in the illustrated example). Here, however, the IOL that is inserted into the near eye is an EDF IOL that adds spherical aberration to the eye. As compared to the near eye in FIG. 1A, the marginal focus has moved away from the paraxial focus in the near eye with the EDF IOL in FIG. 4A, and there is slightly reduced visual acuity at the best focus which is likely clinically insignificant. There is also a clinically significant increase in the depth of focus. This clinically significant increase may be an added line or more of acuity on the near visual acuity test chart. The best potential acuity of the near eye will be less than that of the distance eye, but the depth of focus of the near eye will be greater than that of the distance eye. The increased depth of focus adds about 0.3 D of acceptable near vision as compared to the method illustrated in FIGS. 1A and 1B. As a result, and referring to FIG. 4B, high visually acuity is maintained in the far eye while, as compared to the procedure illustrated in FIGS. 1A and 1B, intermediate vision is improved, and there is better near vision. Put another way, other aspects of the procedure being identical, intermediate and near binocular vision are improved when the EDF IOL is used in the near eye.

The aspheric IOL in the distance eye may, in some implementations, be an achromatic IOL that, in addition to reducing or eliminating spherical aberrations, reduces the chromatic aberrations. For example, a diffractive-refractive hybrid IOL may be employed. Such a lens further increases the potential visual acuity of the distance eye.

In other exemplary implementations similar that described above with reference to FIGS. 4A and 4B, and EDF IOL may be used in both the distance and near eyes in order to increase the depth of focus of both eyes.

Figure 5A:
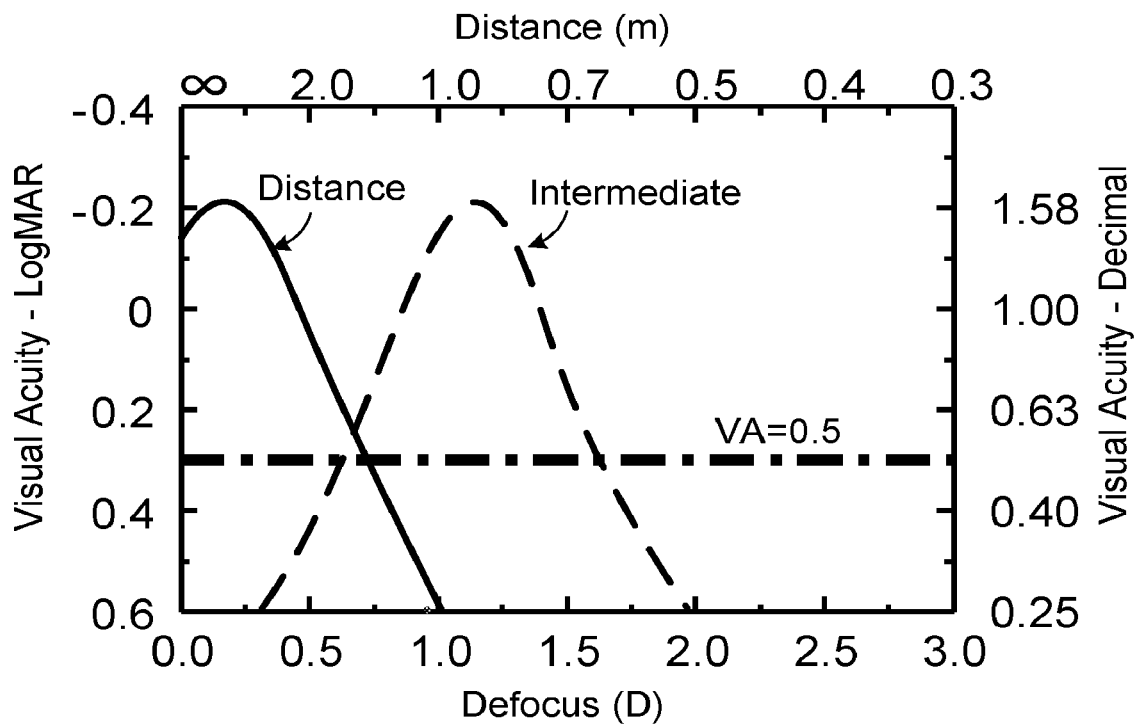
FIG. 5A is a graph showing visual acuity as a function of defocus in each eye after another pseudophakic monovision procedure.
Figure 5B:
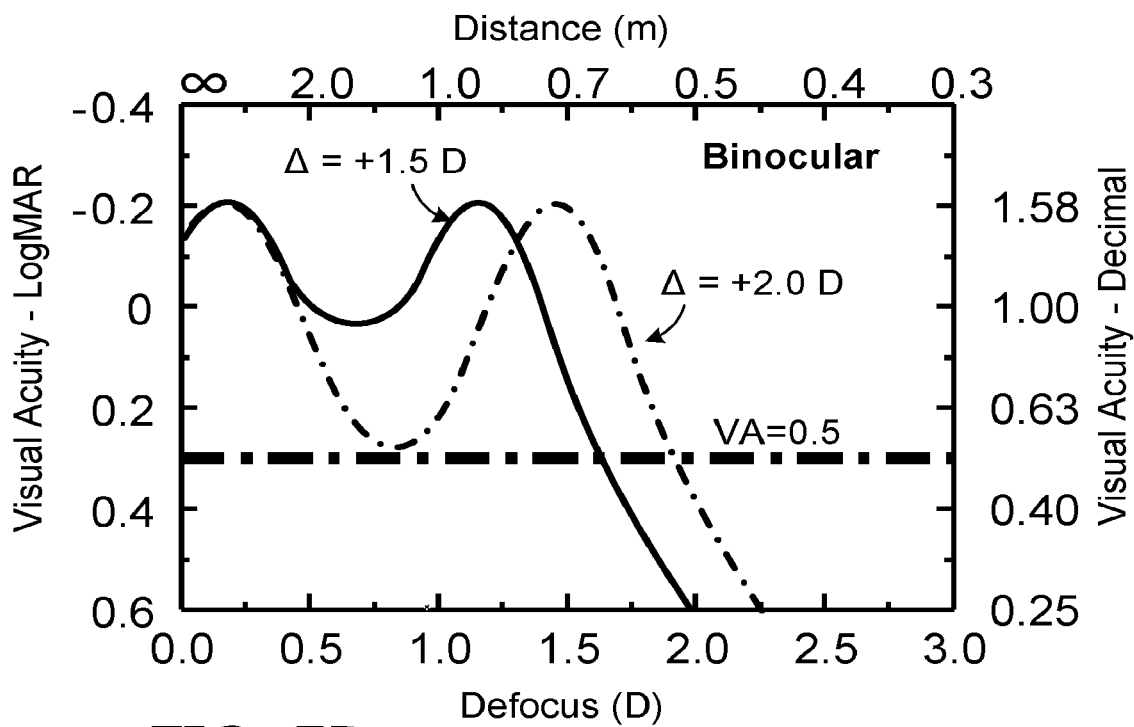
FIG. 5B is a graph showing binocular visual acuity as a function of defocus after the pseudophakic monovision procedure illustrated in FIG. 5A.

As illustrated for example in FIGS. 5A and 5B, an exemplary pseudophakic monovision procedure in accordance with at least some of the present inventions includes setting the vision in one eye for distance vision and the other eye for intermediate vision (instead of near vision as discussed above). An aspheric IOL that eliminates (or at least substantially eliminates) spherical aberration is inserted into distance eye. Unlike the conventional example illustrated in FIGS. 1A and 1B, there is only a modest difference between the distance eye and the other eye and, accordingly, the procedure may be referred to a modest pseudophakic monovision procedure and the other eye may be referred to as the intermediate eye. The IOL that is inserted into the intermediate eye may be about 1.0 to 1.5 D greater, than the IOL for the distance eye (1.5 D more, or Δ=+1.5 D, in the illustrated example). As a result, and referring to FIG. 5B, better visual acuity is maintained for intermediate vision while, as compared to the procedure illustrated in FIGS. 1A and 1B (Δ=+2.0 D), intermediate vision and stereoacuity are markedly improved. Although near vision is not as good, spectacles may be employed, if necessary, for near vision.

The aspheric IOL in the distance eye may, in some implementations, be an achromatic IOL that, in addition to reducing or eliminating spherical aberrations, reduces the chromatic aberrations. For example, a diffractive-refractive hybrid IOL may be employed. Such a lens further increases the visual acuity of the distance eye.

Figure 6A:
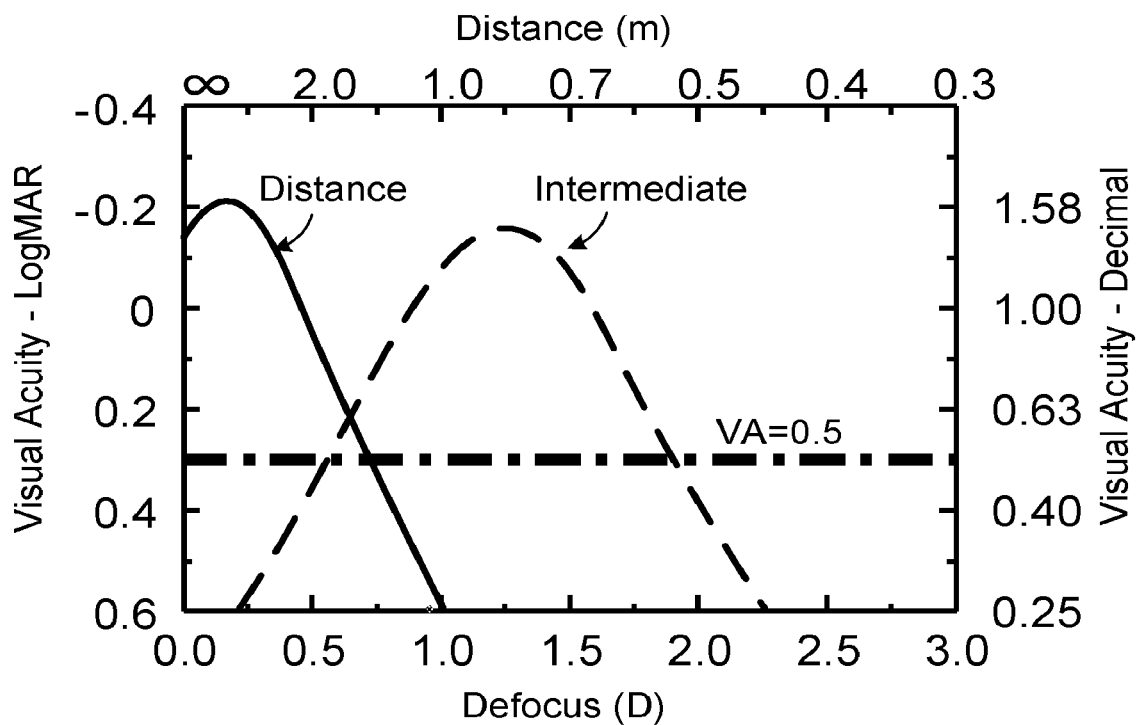
FIG. 6A is a graph showing visual acuity as a function of defocus in each eye after another pseudophakic monovision procedure, in accordance with a present invention, in which the intermediate eye includes an aspheric IOL which adds spherical aberration to the eye.
Figure 6B:
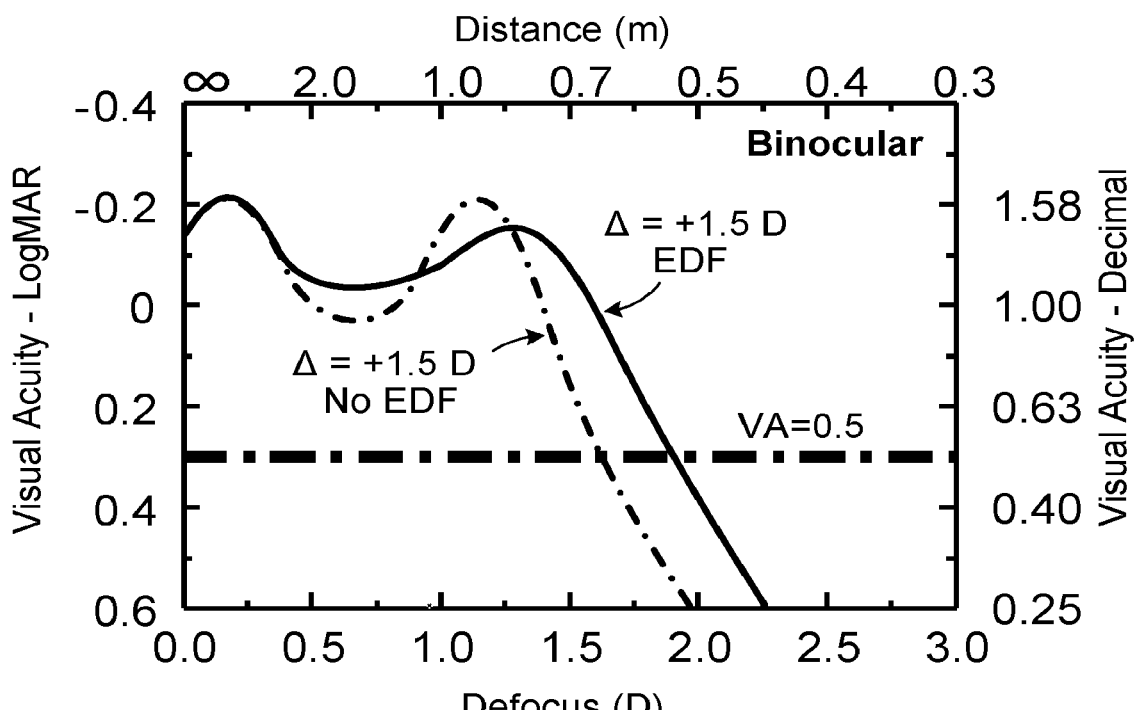
FIG. 6B is a graph showing binocular visual acuity as a function of defocus after the pseudophakic monovision procedure illustrated in FIG. 6A.

Turning to FIGS. 6A and 6B, an EDF IOL may be employed in the intermediate eye in a modest monovision procedure such as that illustrated in FIGS. 5A and 5B. The procedure involves inserting an aspheric IOL that eliminates (or at least substantially eliminates) spherical aberration into distance eye and inserting an IOL into the intermediate eye that may be about 1.0 to 1.5 D greater than the IOL for the distance eye (Δ=+1.5 D in the illustrated example). Here, however, the IOL that is inserted into the intermediate eye is an EDF IOL that adds spherical aberration to the eye. As compared to the intermediate eye in FIG. 5A, the marginal focus of the near eye with the EDF IOL in FIG. 6A has moved away from the paraxial focus and there is less contrast at best focus. There is also an increase in the depth of focus. The visual acuity of the intermediate eye will be slightly less than that of the distance eye, but the depth of focus of the intermediate eye will be greater than that of the distance eye. The increased depth of focus adds about 0.3 D of acceptable near vision. As a result, and referring to FIG. 6B, high binocular visual acuity is maintained in the far eye while, as compared to the procedure illustrated in FIGS. 5A and 5B, intermediate vision is further improved and there is better near vision. Put another way, other aspects of the procedure being identical, intermediate and near binocular vision are improved when the EDF IOL is used in the intermediate eye in a modest monovision procedure.

Figure 1A:
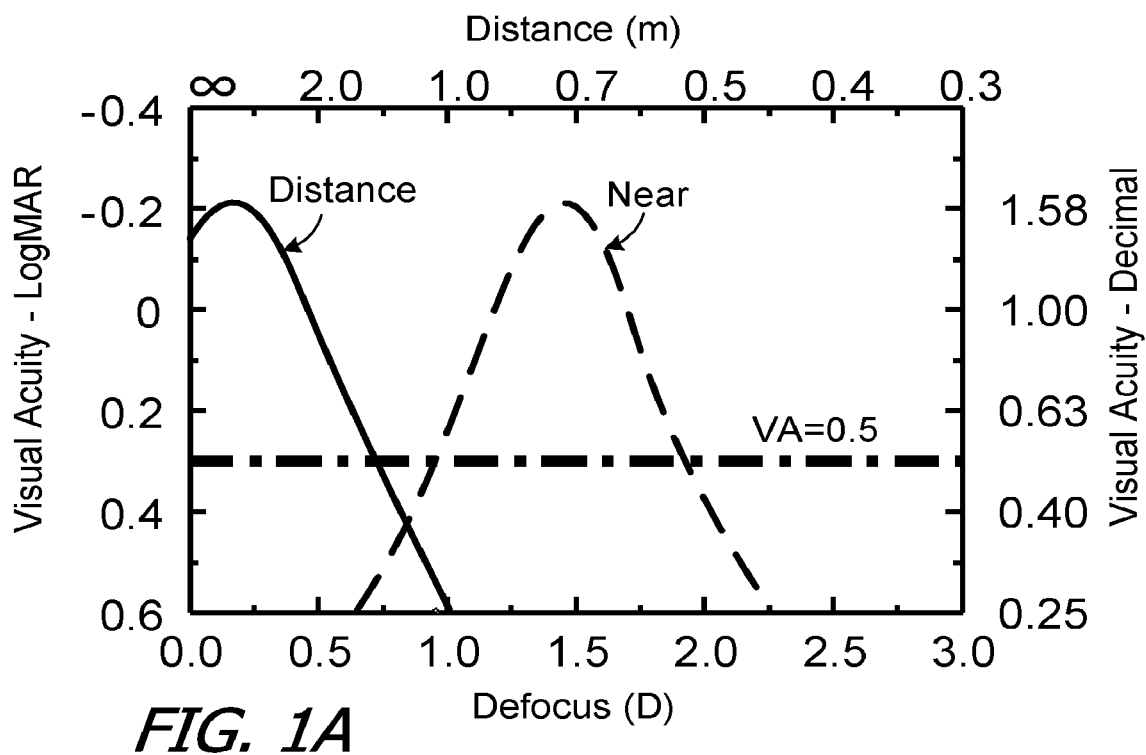
FIG. 1A is a graph showing visual acuity as a function of defocus in each eye after a conventional pseudophakic monovision procedure.
Figure 1B:
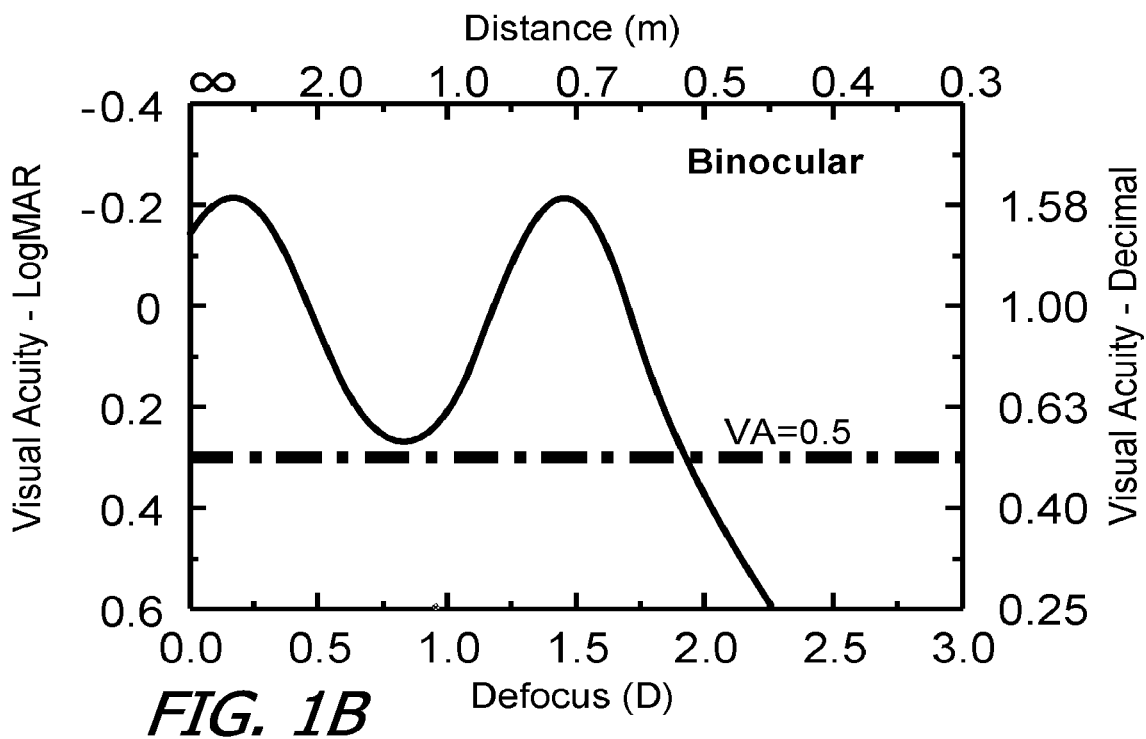
FIG. 1B is a graph showing binocular visual acuity as a function of defocus after the pseudophakic monovision procedure illustrated in FIG. 1A.
Figure 6C:
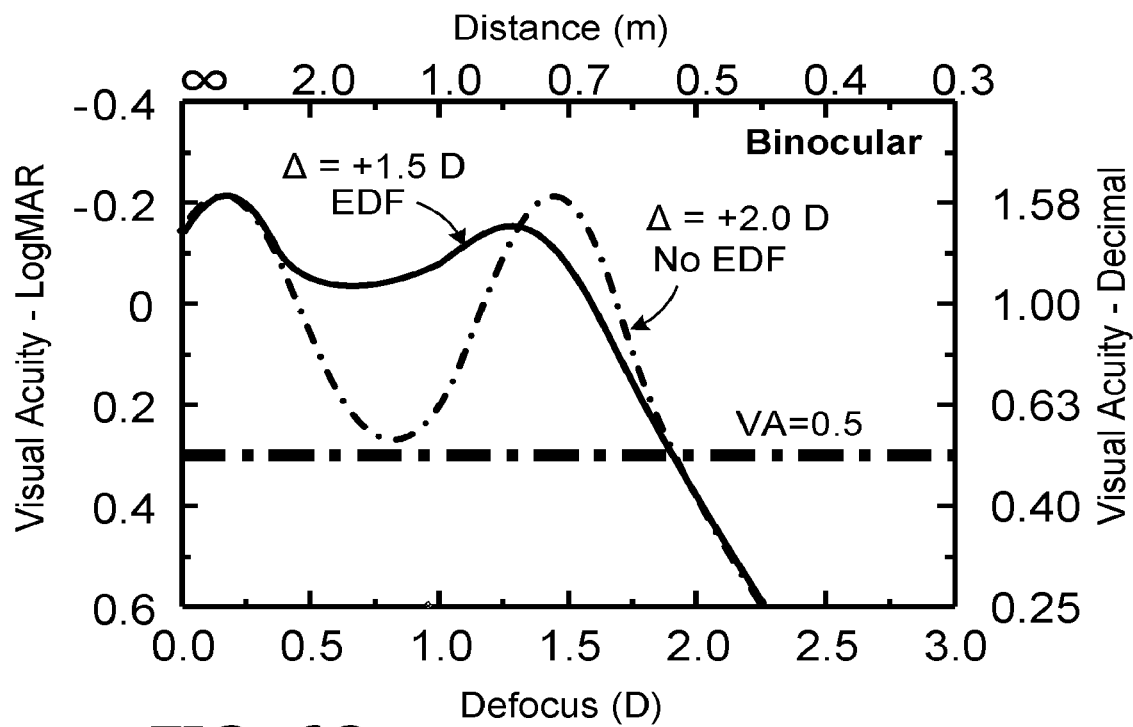
FIG. 6C is a graph showing binocular visual acuity as a function of defocus after the pseudophakic monovision procedures illustrated in FIGS. 1A and 6A.

It should also be noted that modest monovision procedures which employ an EDF IOL are a substantial improvement over conventional monovision procedures such as that illustrated in FIGS. 1A and 1B (Δ=+2.0 D, no EDF). Referring to FIG. 6C, a modest monovision procedure that employs an EDF IOL in the intermediate eye has substantially improved intermediate vision and the same near vision, with a relatively minor loss of visual acuity.

The aspheric IOL in the distance eye in FIGS. 6A and 6B may, in some implementations, be an achromatic IOL that, in addition to reducing or eliminating spherical aberrations, reduces the chromatic aberrations. For example, a diffractive-refractive hybrid IOL may be employed. Such a lens further increases the visual acuity of the distance eye.

In other exemplary implementations similar that described above with reference to FIGS. 6A and 6B, an EDF IOL may be used in both the distance and intermediate eyes in order to increase the depth of focus of both eyes.

EDF IOLs may also be used in other methods. For example, an IOL that is set for distance may be inserted into each of the eyes, with one being an aspheric IOL that eliminates spherical aberration to provide best visual acuity and the other being an EDF IOL that adds spherical aberration to the eye to increase depth of focus. Here too, the aspheric IOL that eliminates spherical aberration may be an achromatic IOL that also eliminates chromatic aberration. Alternatively, an IOL that is set for near vision may be inserted into each of the eyes, with one being an aspheric IOL that eliminates spherical aberration to provide best visual acuity and the other being an EDF IOL that adds spherical aberration to the eye to increase depth of focus. The aspheric IOL that eliminates spherical aberration may be an achromatic IOL that also eliminates chromatic aberration.

In those instances where the patient is not satisfied with the results of the procedures described above, spectacles may be employed that cancel or otherwise alter the effects of the IOLs. This may include situation like driving at night where the added spherical aberration from the EDF IOL is not helpful to best nighttime vision. In those cases, spectacles or contact lenses that will undo or reduce the total spherical aberration of the eye can be worn. Alternatively, EDF IOLs that are configured such that the adverse effects of the spherical (or other higher order) aberration in low light conditions are reduced may be employed. Such EDF IOLs are described below with reference to FIGS. 11A-14.

Figure 6D:
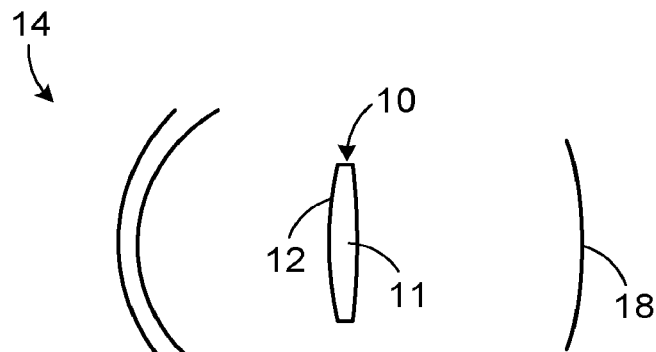
FIG. 6D is a schematic view of an optical system, including an IOL and an eye, in accordance with at least one embodiment of a present invention.

With respect to the EDF IOLs themselves, and as discussed above, the EDF IOLs improve depth of focus by controlling the amount of spherical aberrations of the eye. One such EDF IOL, which is identified by reference numeral 10 in FIG. 6D, has a lens body 11 and an aspheric lens surface 12 to provide the controlled spherical aberrations necessary to achieve the desired depth of focus. Haptics (not shown) may also be provided. Although the aspheric surface 12 is the anterior surface in the illustrated embodiment and the posterior surface is spherical, the posterior surface may, alternatively or in addition, be aspheric. The EDF IOL 10 is shown as part of an optical system that also includes an eye 14 with a cornea 16 and retina 18. A process of designing such an IOL, and the resulting exemplary EDF IOLs, is discussed below. Toric IOLs and contact lenses are other examples of suitable optical devices that may be used to add higher order aberration to the eye in accordance with the present inventions.

Suitable material for the EDF IOL includes, but is not limited to, HOYA AF-1 yellow hydrophobic acrylic material and the discussion below (where appropriate) assumes the use of this material. Other exemplary materials include, but are not limited to, hydrogel and PMMA. Although the present inventions are not so limited, an exemplary set of IOL design specifications (or "requirements") are presented in Table 1.

TABLE 1

Exemplary Design Specifications

| Item | Requirements |
|---|---|
| Lens power | 10.0 to 30.0 D, in 0.5 D increments |
| Lens model platform | Fixed edge thickness of 0.18 mm for center thickness > 0.56 mm or variable edge thickness with fixed center thickness of 0.56 mm if previous condition cannot be achieved. |
| Shape factor | −0.2 to +0.2 |
| Field of view (FOV) | On axis |
| Wavelength | e-ray or 546.074 nm |
| Limited aperture for optimization | 6.0 mm at corneal plane |
| Asphericity | The anterior surface of the lens was an aspheric design which used a function of conic constant combined with $4^{th}$ and $6^{th}$ order aspheric coefficients. The posterior surface of the lens was designed as the spherical surface. |
| Optical performance | Provides at least 1.0 D of pseudo-accommodation at a contrast value of 0.1 and a spatial frequency of 50 c/mm with the hypothetical model eye. |
| Constraints | 1. IOL location: Positioned 4.50 mm from the posterior cornea of the hypothetical model eye<br>2. Focus: Fixed paraxial focus |

A hypothetical model eye having optical properties that are similar to the average human eye (e.g., corneal shape and on-axis performance) may be used to evaluate in-situ performance of the EDF IOL, with the EDF IOL replacing the crystalline lens. One suitable model eye is the Liou and Brennan model eye described in Table 2. Note that pupil semi-diameter may be varied and the values in the areas marked X depend on the IOL dioptric power.

TABLE 2

Optical Surface Data For Exemplary Model Eye

| Surf | Comment | Radius | Thickness | Glass | Semi-Diameter | Conic |
|---|---|---|---|---|---|---|
| OBJ | Object | Infinity | Infinity | | 0.00 | 0.00 |
| 1 | Anterior cornea | 7.77 | 0.50 | 1.376 | 6.00 | −0.18 |
| 2 | Posterior cornea | 6.40 | 3.16 | 1.336 | 6.00 | −0.60 |
| STO | Pupil | Infinity | 1.34 | 1.336 | 1.50 | 0.00 |
| 3 | Anterior IOL | X | X | 1.516 | 3.00 | X |
| 4 | Posterior IOL | X | X | 1.336 | 3.00 | 0.00 |
| IMA | Image plane | −8.10 | — | | Auto | |

The performance simulations discussed below were performed with the ZEMAX® optical design program (ZEMAX Development Corporation). The refractive indexes for optical components were chosen for e-ray (0.546074 μm of wavelength).

The simple lens equation was used to derive the apex radii for the aspheric anterior surface and the radii for the spherical posterior surface:

$$D = \left(\frac{n_{IOL} - n_{aqueous}}{r_a}\right) + \left(\frac{n_{aqueous} - n_{IOL}}{r_p}\right) - \frac{CT}{n_{IOL}}\left(\frac{n_{IOL} - n_{aqueous}}{r_a}\right)\left(\frac{n_{aqueous} - n_{IOL}}{r_p}\right)($$

Where,

D is dioptric power of the lens in aqueous, in D (diopters)

$n_{IOL}$ is the refractive index of the IOL optics material, 1.516 is value used for the lens design $n_{aqueous}$ is the refractive index of the IOL surrounding material, 1.336 is value used for the lens design $r_a$ is the radius curvature of the anterior surface of the IOL, in meters $r_p$ is the radius curvature of the posterior surface of the IOL, in meters CT is the center thickness of the IOL, in meters The shape factor was calculated as follows:

$$\text{Shape Factor} = \frac{(r_a + r_p)}{(r_a - r_p)}$$

The asphericity of the anterior surface of the optics was optimized using ZEMAX® optical design program in the model eye discussed above (Table 2). The merit function used for optimizing the lens design is the longitudinal aberration. Table 3 lists a pre-defined longitudinal spherical aberration to improve the depth of focus for 20.0 D IOL power, where the Zone is the NRD (discussed below) and the Target is the longitudinal spherical aberration (LSA) in mm:

TABLE 3

Pre-Defined Longitudinal Spherical Aberration
(Variables for ZEMAX ® Merit Function)

| Zone | Target | Zone | Target | Zone | Target | Zone | Target |
|---|---|---|---|---|---|---|---|
| 0.00 | 0.000 | 0.26 | −0.069 | 0.52 | −0.276 | 0.78 | −0.620 |
| 0.02 | 0.000 | 0.28 | −0.080 | 0.54 | −0.297 | 0.80 | −0.653 |
| 0.04 | −0.002 | 0.30 | −0.092 | 0.56 | −0.320 | 0.82 | −0.686 |
| 0.06 | −0.004 | 0.32 | −0.104 | 0.58 | −0.343 | 0.84 | −0.720 |
| 0.08 | −0.007 | 0.34 | −0.118 | 0.60 | −0.367 | 0.86 | −0.754 |
| 0.10 | −0.010 | 0.36 | −0.132 | 0.62 | −0.392 | 0.88 | −0.790 |
| 0.12 | −0.015 | 0.38 | −0.147 | 0.64 | −0.418 | 0.90 | −0.826 |
| 0.14 | −0.020 | 0.40 | −0.163 | 0.66 | −0.444 | 0.92 | −0.863 |
| 0.16 | −0.026 | 0.42 | −0.180 | 0.68 | −0.472 | 0.94 | −0.901 |
| 0.18 | −0.033 | 0.44 | −0.197 | 0.70 | −0.500 | 0.96 | −0.940 |
| 0.20 | −0.041 | 0.46 | −0.216 | 0.72 | −0.529 | 0.98 | −0.979 |
| 0.22 | −0.049 | 0.48 | −0.235 | 0.74 | −0.558 | 1.00 | −1.020 |
| 0.24 | −0.059 | 0.50 | −0.255 | 0.76 | −0.589 | | |

The longitudinal spherical aberration of IOL power other than 20.0 D will be calculated by the following equations:

$$\Delta P_{20} = \frac{1}{EFL_{20} + LSA_{20}} - \frac{1}{EFL_{20}} \quad (3)$$

$$LSA = \frac{1}{P_O + \Delta P_{20}} - \frac{1}{P_O} \quad (4)$$

Where, $\Delta P_{20}$ is amount of defocus of the hypothetical model eye for 20.0 D IOL dioptric power $EFL_{20}$ is the effective focal length of the hypothetical model eye for 20.0 D IOL dioptric power $LSA_{20}$ is the longitudinal spherical aberration of the hypothetical model eye for 20.0 D IOL dioptric power LSA is the longitudinal spherical aberration of the hypothetical model eye $P_O$ is the refractive power of the hypothetical model eye Depth of focus was evaluated using the hypothetical model eye with three different cornea simulations to cover the cornea aberration distribution range.

Figure 7:
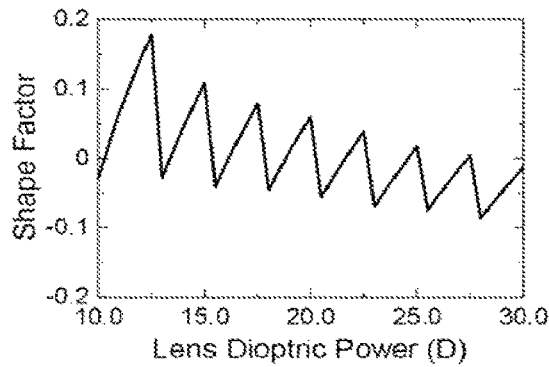
FIG. 7 is a graph showing shape factor as a function of lens dioptric power for an IOL in accordance with one embodiment of a present invention and a conventional spherical IOL.

The simple lens equation was used to derive the apex radii of the aspheric anterior surface and the radii of the spherical posterior surface. The total power range from 10.0 to 30.0 D was divided into 8 bands with the power ranges 10.0 to 12.5 D, 13.0 to 15.0 D, 15.5 to 17.5 D, 18.0 to 20.0 D, 20.5 to 22.5 D, 23.0 to 25.0 D, 25.5 to 27.5 D, and 28.0 to 30.0 D. The anterior apex radius was fixed within one band and the posterior radius was then calculated using the known lens power, edge thickness or center thickness, refractive index of the material, and refractive index of the aqueous. To satisfy the design requirements for shape factor, the fixed anterior apex radius was initially estimated and then adjusted within each of the 8 bands. The shape factor distribution result is shown in FIG. 7.

The design results for the radii design and shape factor are shown in Table 4 for the lens power range of 10.0 to 30.0 D with 0.5 D increments. For the aspheric portion of the design, the anterior apex radius was fixed and then the conic constant was optimized, then higher order aspheric coefficients of 4th order and 6th order were optimized to meet the aberration requirements for each band. Accordingly, the center thickness or the edge thickness was recalculated by changing the anterior surface, which incorporates the asphericity. The ZEMAX® optical design program was used for the aspheric design of the anterior surface. The system was set as 6.0 mm entrance pupil diameter, which is equivalent to about 5.1 mm at the anterior surface of the IOL. The focal point of the system was constrained at the paraxial focus, while the aspheric parameters of the IOL anterior surface were the only variable adjusted. The merit function for the optimization was the longitudinal aberration. In its optimization cycle, ZEMAX® systematically adjusted the aspheric coefficients until a lowest possible value for the merit function was reached. The procedure for running the optimization is described in the ZEMAX® User's Guide.

TABLE 4

Lens Radii, Shape Factors Thicknesses

| IOL Labeled Power (D) | Ant. Apex (mm) | Post. Radius (mm) | Shape Factor | Center Thickness (mm) | Edge Thickness (mm) |
|---|---|---|---|---|---|
| 10.0 | 35.00 | −36.9884 | −0.0276 | 0.5600 | 0.2411 |
| 10.5 | 35.00 | −33.5362 | 0.0214 | 0.5600 | 0.2285 |
| 11.0 | 35.00 | −30.6733 | 0.0659 | 0.5600 | 0.2159 |
| 11.5 | 35.00 | −28.2608 | 0.1065 | 0.5600 | 0.2033 |
| 12.0 | 35.00 | −26.2001 | 0.1438 | 0.5600 | 0.1906 |
| 12.5 | 35.00 | −24.4195 | 0.1781 | 0.5600 | 0.1780 |
| 13.0 | 26.90 | −28.4689 | −0.0283 | 0.5597 | 0.1800 |
| 13.5 | 26.90 | −26.3768 | 0.0098 | 0.5723 | 0.1800 |
| 14.0 | 26.90 | −24.5709 | 0.0453 | 0.5850 | 0.1800 |
| 14.5 | 26.90 | −22.9963 | 0.0782 | 0.5977 | 0.1800 |
| 15.0 | 26.90 | −21.6112 | 0.1090 | 0.6104 | 0.1800 |
| 15.5 | 22.30 | −24.1583 | −0.0400 | 0.6188 | 0.1800 |
| 16.0 | 22.30 | −22.6332 | −0.0074 | 0.6315 | 0.1800 |
| 16.5 | 22.30 | −21.2891 | 0.0232 | 0.6443 | 0.1800 |
| 17.0 | 22.30 | −20.0955 | 0.0520 | 0.6570 | 0.1800 |
| 17.5 | 22.30 | −19.0285 | 0.0792 | 0.6698 | 0.1800 |
| 18.0 | 19.10 | −20.9064 | −0.0452 | 0.6789 | 0.1800 |
| 18.5 | 19.10 | −19.7530 | −0.0168 | 0.6917 | 0.1800 |
| 19.0 | 19.10 | −18.7201 | 0.0100 | 0.7045 | 0.1800 |
| 19.5 | 19.10 | −17.7898 | 0.0355 | 0.7173 | 0.1800 |
| 20.0 | 19.10 | −16.9474 | 0.0597 | 0.7302 | 0.1800 |
| 20.5 | 16.60 | −18.5470 | −0.0554 | 0.7395 | 0.1800 |
| 21.0 | 16.60 | −17.6324 | −0.0302 | 0.7524 | 0.1800 |
| 21.5 | 16.60 | −16.8035 | −0.0061 | 0.7653 | 0.1800 |
| 22.0 | 16.60 | −16.0489 | 0.0169 | 0.7782 | 0.1800 |
| 22.5 | 16.60 | −15.3591 | 0.0388 | 0.7911 | 0.1800 |
| 23.0 | 14.60 | −16.7632 | −0.0690 | 0.8006 | 0.1800 |
| 23.5 | 14.60 | −16.0112 | −0.0461 | 0.8135 | 0.1800 |
| 24.0 | 14.60 | −15.3237 | −0.0242 | 0.8265 | 0.1800 |

TABLE 4-continued

Lens Radii, Shape Factors Thicknesses

| IOL Labeled Power (D) | Ant. Apex (mm) | Post. Radius (mm) | Shape Factor | Center Thickness (mm) | Edge Thickness (mm) |
|---|---|---|---|---|---|
| 24.5 | 14.60 | −14.6926 | −0.0032 | 0.8395 | 0.1800 |
| 25.0 | 14.60 | −14.1114 | 0.0170 | 0.8525 | 0.1800 |
| 25.5 | 13.10 | −15.1919 | −0.0739 | 0.8615 | 0.1800 |
| 26.0 | 13.10 | −14.5706 | −0.0531 | 0.8746 | 0.1800 |
| 26.5 | 13.10 | −13.9980 | −0.0331 | 0.8876 | 0.1800 |
| 27.0 | 13.10 | −13.4685 | −0.0139 | 0.9007 | 0.1800 |
| 27.5 | 13.10 | −12.9775 | 0.0047 | 0.9139 | 0.1800 |
| 28.0 | 11.80 | −13.9954 | −0.0851 | 0.9229 | 0.1800 |
| 28.5 | 11.80 | −13.4653 | −0.0659 | 0.9360 | 0.1800 |
| 29.0 | 11.80 | −12.9738 | −0.0474 | 0.9492 | 0.1800 |
| 29.5 | 11.80 | −12.5168 | −0.0295 | 0.9624 | 0.1800 |
| 30.0 | 11.80 | −12.0907 | −0.0122 | 0.9757 | 0.1800 |

Table 5 (below) is an example of the prescription of the model eye with a 21.5 D IOL used for the optimization. Since each band used only one universal anterior aspheric design, the optimizations were only done for the mid-power in each band, i.e. 11.5 D, 14.0 D, 16.5 D, 19.0 D, 21.5 D, 24.0 D, 26.5 D, and 29.0 D. The optical performance was checked at two extremes of the band to make sure the criteria were still maintained.

General Lens Data:
Surfaces: 10
Stop: 4
System Aperture: Float By Stop Size=1.5
Glass Catalogs: SCHOTT
Ray Aiming: Paraxial Reference, Cache On
X Pupil shift: 0
Y Pupil shift: 0
Z Pupil shift: 0
X Pupil compress: 0
Y Pupil compress: 0
Apodization: Uniform, factor=0.00000E+000
Temperature (C): 2.00000E+001
Pressure (ATM): 1.00000E+000
Adjust Index Data To Environment: Off
Effective Focal Length: 16.64387 (in air at system temperature and pressure)
Effective Focal Length: 16.64387 (in image space)
Back Focal Length: 1.804532e-015
Total Track: 23.86947
Image Space F/#: 4.895964
Paraxial Working F/#: 4.895964
Working F/#: 4.813402
Image Space NA: 0.1015965
Object Space NA: 1.699754e-010
Stop Radius: 1.5
Paraxial Image Height: 0
Paraxial Magnification: 0
Entrance Pupil Diameter: 3.399508
Entrance Pupil Position: 3.0981
Exit Pupil Diameter: 3.083149
Exit Pupil Position: −15.09498
Field Type: Angle in degrees
Maximum Radial Field: 0
Primary Wavelength 0.546074 pm
Lens Units: Millimeters
Angular Magnification: 0
Fields: 1
Field Type: Angle in degrees

| # | X-Value | Y-Value | Weight |
|---|---|---|---|
| 1 | 0.000000 | 0.000000 | 1.000000 |

Vignetting Factors

| # | VDX | VDY | VCX | VCY | VAN |
|---|---|---|---|---|---|
| 1 | 0.000000 | 0.000000 | 0.000000 | 0.000000 | 0.000000 |

Wavelengths: 1
Units: jm

| # | Value | Weight |
|---|---|---|
| 1 | 0.546074 | 1.000000 |

Surface Data Summary:

TABLE 5

(Part 1)-Exemplary Prescription (IOL 21.5 D)

| Surf | Type | Radius | Thickness | Glass | Diameter | Conic | Comment |
|---|---|---|---|---|---|---|---|
| OBJ | STANDARD | Infinity | Infinity | | | 0 | Object Distance |
| 1 | STANDARD | Infinity | 0 | | 3.38444 | 0 | |
| 2 | STANDARD | 7.77 | 0.5 | 1.376000, 0.000000 | 10 | | −0.18 Cornea |
| Anterior | | | | | | | |
| 3 | STANDARD | 6.4 | 3.16 | 1.336000, 0.000000 | 10 | | −0.6 Cornea |
| Posterior | | | | | | | |
| STO | STANDARD | Infinity | 1.34 | 1.336000, 0.000000 | 3 | 0 | Pupil |
| 5 | COORDBRK | | 0 | | — | — | Element Tilt |
| 6 | EVENASPH | 16.6 | 0.7652811 | 1.516000, 0.000000 | 6 | 13.67134 | IOL Anterior |
| 7 | STANDARD | −16.80351 | −0.7652811 | 1.336000, 0.000000 | 6 | 0 | IOL Posterior |

TABLE 5-continued (Part 1)-Exemplary Prescription (IOL 21.5 D)

| Surf | Type | Radius | Thickness | Glass | Diameter | Conic | Comment |
|---|---|---|---|---|---|---|---|
| 8 | COORDBRK | | 0.7652811 | — | | — | Element Tilt |
| 9 | STANDARD | Infinity | 18.10419 | 1.336000, 0.000000 | 2.762625 | 0 | Dummy |
| IMA | STANDARD | Infinity | | | 0.06119537 | 0 | |

Surface Data Detail:
Surface OBJ: STANDARD Object Distance
Surface1: STANDARD
Surface 2: STANDARD Cornea Anterior
Aperture: Floating Aperture
Maximum Radius: 5
Surface 3: STANDARD Cornea Posterior
Aperture: Floating Aperture
Maximum Radius: 5
Surface STD: STANDARD Pupil
Surface 5: COORDBRK Element Tilt
Decenter X: 0
Decenter Y: 0
Tilt About X: 0
Tilt About Y: 0
Tilt About Z: 0
Order: Decenter then tilt
Surface6: EVENASPH IOL Anterior
Coeff on r 2: 0
Coeff on r 4: −1.58969856-005
Coeff on r 6: 2.3213549e-006
Coeff on r 8: 0
Coeff on r 10: 0
Coeff on r 12: 0
Coeff on r 14: 0
Coeff on r 16: 0
Aperture: Floating Aperture
Maximum Radius: 3
Surface 7: STANDARD IOL Posterior
Aperture: Floating Aperture
Maximum Radius: 3
Surface 8: COORDBRK Element Tilt
Decenter X: 0
Decenter Y: 0
Tilt About X: 0
Tilt About Y: 0
Tilt About Z: 0
Order: Tilt then decenter
Surface 9: STANDARD Dummy
Surface IMA: STANDARD
Edge Thickness Data:

TABLE 5

(Part 2)-Exemplary Prescription (IOL 21.5 D)

| Surf | X-Edge | Y-Edge |
|---|---|---|
| 1 | 1.775001 | 1.775001 |
| 2 | 0.814571 | 0.814571 |
| 3 | 1.070428 | 1.070428 |
| STO | 1.340000 | 1.340000 |
| 5 | 0.315311 | 0.315311 |
| 6 | 0.180000 | 0.180000 |
| 7 | −0.495311 | −0.495311 |
| 8 | 0.765281 | 0.765281 |
| 9 | 18.104185 | 18.104185 |
| IMA | 0.000000 | 0.000000 |

Index of Refraction Data:
System Temperature: 20.0000 Celsius
System Pressure: 1.0000 Atmospheres
Absolute air index: 1.000273 at wavelength 0.546074 pm
Index data is relative to air at the system temperature and pressure.
Wavelengths are measured in air at the system temperature and pressure.

TABLE 5

(Part 3)-Exemplary Prescription (IOL 21.5 D)

| Surf | Glass | Temp | Pres | 0.546074 |
|---|---|---|---|---|
| 0 | | 20.00 | 1.00 | 1.00000000 |
| 1 | | 20.00 | 1.00 | 1.00000000 |
| 2 | <MODEL> | 20.00 | 1.00 | 1.37600000 |
| 3 | <MODEL> | 20.00 | 1.00 | 1.33600000 |
| 4 | <MODEL> | 20.00 | 1.00 | 1.33600000 |
| 5 | <CRD BRK> | | | 1.33600000 |
| 6 | <MODEL> | 20.00 | 1.00 | 1.51600000 |
| 7 | <MODEL> | 20.00 | 1.00 | 1.33600000 |
| 8 | <CRD BRK> | | | 1.33600000 |
| 9 | <MODEL> | 20.00 | 1.00 | 1.33600000 |
| 10 | | 20.00 | 1.00 | 1.00000000 |

The aspheric profile design ended up as a paraboloid with higher even order aspheric coefficients. The sag value of the even asphere surface is described by:

$$z(r) = \frac{cr^2}{1+\sqrt{1-(1+k)c^2r^2}} + \alpha_2 r^4 + \alpha_3 r^6$$

Where,
c is the curvature (the reciprocal of the radius)
r—is the radial coordinate in lens unit
k is the conic constant
$a_i$ is the coefficients of the polynomial terms
The conic constant and higher order coefficients, for each band, are presented in Table 6 (below).

TABLE 6

Exemplary Aspheric Coefficients for Each Band

| Mid-power in each band (D) | Even Asphere Coefficients | | |
|---|---|---|---|
| | Conic | 4th order | 6th order |
| 11.5 | 125.03833460 | 3.058827529e−004 | −4.096486219e−005 |
| 14.0 | 59.28198624 | 9.809206013e−005 | −1.345576419e−005 |
| 16.5 | 34.57907429 | 4.715756801e−005 | −6.520266613e−006 |
| 19.0 | 21.52098130 | 1.066288901e−005 | −1.439544636e−006 |
| 21.5 | 13.67134025 | −1.589698480e−005 | 2.321354864e−006 |
| 24.0 | 8.79889408 | −3.428245978e−005 | 4.962644847e−006 |
| 26.5 | 5.80467318 | −4.483144804e−005 | 6.499747062e−006 |
| 29.0 | 3.76510107 | −4.951921711e−005 | 7.199855047e−006 |

Figure 8:
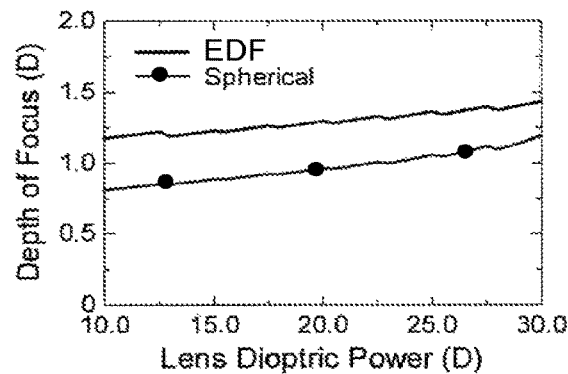
FIG. 8 is a graph showing defocus as a function of lens dioptric power for an IOL in accordance with one embodiment of a present invention and a conventional spherical IOL.
Figure 9A:
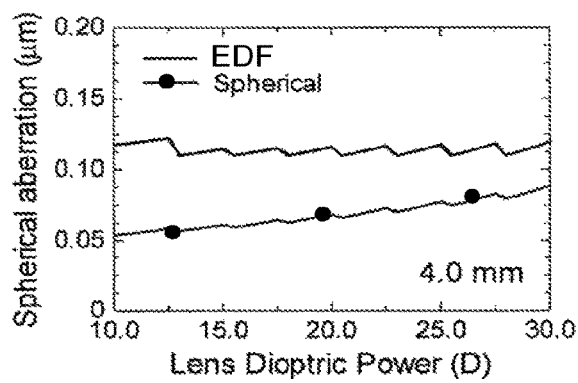
FIGS. 9A and 9B are graphs showing spherical aberration as a function of lens dioptric power for an IOL in accordance with one embodiment of a present invention and a conventional spherical IOL.
Figure 9B:
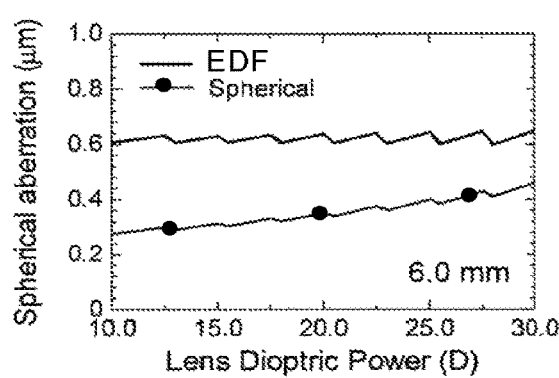

The EDF IOL, with its improved depth of focus, allows the system to reach at least 1.0 D amount of defocus performance across the designed power range. FIGS. 8, 9A and 9B are plots of system depth of focus and total spherical aberration for the IOL power from 10.0 to 30.0 D. The numerical data for these plots is shown in Table 7 (below). Despite concerns that a banded anterior platform design would degrade the performance of the lens at the outer limits of the band compared to the lens in the center of the band (best optimized lens), the data showed that the degradation was not significant. This is likely due to the benefit of using a narrow bandwidth. Across the entire power range illustrated in FIG. 8, the minimum depth of focus was 1.18 D (with a mean of 1.29 D and SD 0.07 D) at 3.0 mm pupil size, which was significantly better than the minimum depth of focus with spherical IOL of 0.81 D. Turning to FIGS. 9A and 9B, the mean spherical aberration was 0.1143 µm (with a minimum of 0.1099 µm, a maximum of 0.1221 µm, and SD 0.0034 µm) at 4.0 mm entrance pupil and 0.6215 µm (with a minimum of 0.5993 µm, a maximum of 0.6497 µm, and SD 0.0129 µm) at 6.0 mm entrance pupil, which was significantly higher than the mean spherical aberration with spherical IOL of 0.0683 µm at 4.0 mm entrance pupil and 0.3517 µm at 6.0 mm entrance pupil.

TABLE 7

Predicted Optical Performance after IOL is Aspherized

| IOL Labeled Power (D) | Depth of Focus (D) | | Spherical Aberration Z40 (µm) | | | |
|---|---|---|---|---|---|---|
| | EDF | Spherical | EDF (4.0 mm) | EDF (6.0 mm) | Spherical (4.0 mm) | Spherical (6.0 mm) |
| 10.0 | 1.175 | 0.813 | 0.1175 | 0.6076 | 0.0540 | 0.2767 |
| 10.5 | 1.184 | 0.821 | 0.1183 | 0.6118 | 0.0548 | 0.2807 |
| 11.0 | 1.193 | 0.828 | 0.1192 | 0.6163 | 0.0556 | 0.2850 |
| 11.5 | 1.202 | 0.836 | 0.1201 | 0.6211 | 0.0565 | 0.2897 |
| 12.0 | 1.211 | 0.843 | 0.1211 | 0.6263 | 0.0575 | 0.2947 |
| 12.5 | 1.221 | 0.851 | 0.1221 | 0.6318 | 0.0585 | 0.3000 |
| 13.0 | 1.188 | 0.852 | 0.1102 | 0.6070 | 0.0569 | 0.2916 |
| 13.5 | 1.197 | 0.860 | 0.1112 | 0.6122 | 0.0579 | 0.2967 |
| 14.0 | 1.208 | 0.867 | 0.1123 | 0.6178 | 0.0589 | 0.3021 |
| 14.5 | 1.217 | 0.877 | 0.1134 | 0.6237 | 0.0600 | 0.3079 |
| 15.0 | 1.227 | 0.885 | 0.1146 | 0.6300 | 0.0612 | 0.3140 |
| 15.5 | 1.220 | 0.886 | 0.1102 | 0.6075 | 0.0596 | 0.3056 |
| 16.0 | 1.229 | 0.894 | 0.1114 | 0.6136 | 0.0607 | 0.3116 |
| 16.5 | 1.240 | 0.904 | 0.1126 | 0.6202 | 0.0619 | 0.3179 |
| 17.0 | 1.250 | 0.912 | 0.1139 | 0.6271 | 0.0632 | 0.3247 |
| 17.5 | 1.261 | 0.922 | 0.1153 | 0.6344 | 0.0646 | 0.3318 |
| 18.0 | 1.250 | 0.921 | 0.1101 | 0.6066 | 0.0627 | 0.3221 |
| 18.5 | 1.261 | 0.930 | 0.1115 | 0.6138 | 0.0641 | 0.3291 |
| 19.0 | 1.272 | 0.941 | 0.1129 | 0.6214 | 0.0655 | 0.3366 |
| 19.5 | 1.284 | 0.951 | 0.1144 | 0.6294 | 0.0670 | 0.3444 |
| 20.0 | 1.294 | 0.962 | 0.1160 | 0.6379 | 0.0685 | 0.3527 |
| 20.5 | 1.282 | 0.958 | 0.1100 | 0.6051 | 0.0662 | 0.3405 |
| 21.0 | 1.294 | 0.969 | 0.1116 | 0.6134 | 0.0678 | 0.3486 |
| 21.5 | 1.306 | 0.981 | 0.1132 | 0.6220 | 0.0694 | 0.3571 |
| 22.0 | 1.317 | 0.993 | 0.1149 | 0.6312 | 0.0711 | 0.3661 |
| 22.5 | 1.329 | 1.007 | 0.1167 | 0.6408 | 0.0728 | 0.3755 |
| 23.0 | 1.312 | 0.999 | 0.1099 | 0.6033 | 0.0701 | 0.3608 |
| 23.5 | 1.325 | 1.011 | 0.1117 | 0.6127 | 0.0718 | 0.3700 |
| 24.0 | 1.338 | 1.025 | 0.1135 | 0.6225 | 0.0736 | 0.3796 |
| 24.5 | 1.351 | 1.040 | 0.1154 | 0.6328 | 0.0755 | 0.3897 |
| 25.0 | 1.364 | 1.056 | 0.1174 | 0.6436 | 0.0775 | 0.4003 |
| 25.5 | 1.343 | 1.045 | 0.1100 | 0.6013 | 0.0747 | 0.3854 |
| 26.0 | 1.358 | 1.060 | 0.1119 | 0.6118 | 0.0766 | 0.3957 |
| 26.5 | 1.372 | 1.077 | 0.1140 | 0.6229 | 0.0786 | 0.4066 |
| 27.0 | 1.385 | 1.096 | 0.1161 | 0.6345 | 0.0808 | 0.4181 |
| 27.5 | 1.399 | 1.117 | 0.1183 | 0.6466 | 0.0830 | 0.4300 |
| 28.0 | 1.375 | 1.096 | 0.1101 | 0.5993 | 0.0796 | 0.4116 |
| 28.5 | 1.390 | 1.116 | 0.1123 | 0.6110 | 0.0817 | 0.4232 |
| 29.0 | 1.405 | 1.138 | 0.1145 | 0.6234 | 0.0840 | 0.4354 |
| 29.5 | 1.420 | 1.163 | 0.1169 | 0.6362 | 0.0863 | 0.4481 |
| 30.0 | 1.435 | 1.193 | 0.1193 | 0.6497 | 0.0888 | 0.4614 |

The depth of focus of the EDF IOL was compared to that of a typical spherical IOL using the hypothetical model eye via computer simulation to determine the effects of corneal aberration distribution.

Considering the broad population distribution of inherent cornea spherical aberration in human eyes, the image quality of the EDF IOL was evaluated using the hypothetical model eye with corneas having a range of aberrations. Lenses were evaluated for modulation transfer function (MTF) through-focus-response performance using the hypothetical model eye and ±0.1 µm spherical aberration. Corneal spherical aberration was modeled by adjusting the conic constant of the anterior cornea surface. Table 8 lists the parameters used for these model corneas.

TABLE 8

Model Parameters

| | Mean SA Cornea − 0.1 µm | Mean SA Cornea | Mean SA Cornea + 0.1 µm |
|---|---|---|---|
| SA Cornea | 0.164 µm | 0.264 µm | 0.364 µm |
| Anterior Conic Constant | −0.326 | −0.180 | −0.038 |

The EDF IOL and spherical IOL used in the simulation were 21.5 D, and they both had the same apex anterior radius and posterior radius, except that the EDF IOL had an aspheric profile added to its anterior side. The MTF through-focus-response at a spatial frequency of 50 c/mm were evaluated with 3.0 mm pupil size, and the amount of depth of focus were calculated from the main-lobe width at a contrast value of 0.1 with the hypothetical model eye.

The EDF IOL and spherical IOL did not experience dramatic performance changes with the two deviated spherical aberration (SA) corneas compared to that of the mean hypothetical cornea. The pseudo-accommodation values for the EDF IOL at ranged from 1.306 D (at mean SA) to 1.202

(at mean SA−0.1 μm) and 1.351 (at mean SA+0.1 μm). While for a spherical IOL, the pseudo-accommodation values ranged from 0.981 (at mean SA) to 0.927 (at mean SA −0.1 μm) and 1.120 (at mean SA+0.1 μm). The pseudo-accommodation values for the EDF IOL are still above 1.0 D for all situations.

The lens placement errors to be evaluated, including tilt and decentration, were adopted from the ISO standards. A ZEMAX® model was set up to simulate how the image quality degrades with IOL tilt and decentration. The MTF values at 50 c/mm are calculated for 3.0 mm pupil as a function of tilt and decentration values. The image quality of the system degrades with increasing tilt angle, however, within a certain range, e.g., up to 6 degrees, the EDF IOL performs not less than 0.1 contrast degradation. The image quality of the system degrades with increasing decentration, however, within a certain range, e.g., up to 0.5 mm, the EDF IOL still performs not less than 0.1 contrast degradation.

Turning to the correction of chromatic aberration, best vision for the far vision eye can be achieved by correcting all corneal aberrations, including chromatic aberration due to the dispersiveness of the cornea. A pseudophakic IOL with a diffractive-refractive hybrid design can be used to correct chromatic aberration.

By utilizing the properties of Abbe number of refractive and diffractive design which has opposite sign, the diffractive-refractive hybrid achromatic IOL design can be readily realized. The total power of hybrid IOL may be defined as $$\frac{1}{f} = \frac{1}{f_{ref}} + \frac{1}{f_{dif}}$$

where $$\frac{1}{f_{ref}} \text{ and } \frac{1}{f_{dif}}$$

are the refractive and diffractive power of the lens, respectively,

The chromatic aberration for given Abbe number will vanish by the following condition:

$$\frac{1}{f_{ref} v_{e\_ref}} + \frac{1}{f_{dif} v_{e\_dif}} = 0$$

where $v_{e\_ref}$ and $v_{e\_dif}$ are the Abbe number of refractive and diffractive, respectively.

Figure 10:
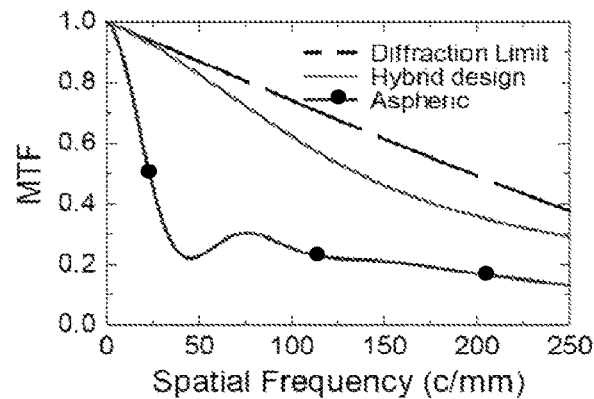
FIG. 10 is a graph showing MTF and a function of spatial frequency.

The diffractive-refractive hybrid achromatic lens can be optimized by ZEMAX® optical design program. FIG. 10 shows the polychromatic modulation transfer function (MTF) of the ocular system at 4.0 mm as the result of ZEMAX optimization for diffractive-refractive hybrid achromat IOL. It was clear that although the MTF of the diffractive-refractive hybrid achromat IOL didn't reach the diffraction limit, the MTF is dramatically better than a conventional aspheric IOL.

The present inventors have determined that it would be desirable to increase the level of higher order aberrations (e.g., spherical, trefoil or coma) added to an eye with an EDF IOL or other optical device, as compared to the EDF IOLs and optical devices described above, to further improve depth of focus in that eye and to further improve intermediate and near binocular vision. For example, in some implementations, an aspheric EDF IOL may be inserted into the eye (e.g., the near eye in a monovision or modest monovision procedure) to add more spherical aberration to the eye than that which is described above to further increase depth of focus in that eye. The present inventors have also determined that although the increase in depth of focus is beneficial, especially in bright daylight and indoor light conditions, the increase in spherical aberration (or other higher order aberration) leads to an increased (and sometimes unacceptable) level of image degradation in low light conditions (e.g., driving at night). The use of additional spherical aberration in the near eye in a modest monovision procedure is illustrative. In bright daylight conditions, where pupil diameter is relatively small (e.g., less than 3 mm) and focus is typically on objects in the distance, the additional spherical aberration in the near eye is minimized, although depth of focus is enhanced. In indoor light, where pupil diameter is a bit larger (e.g., about 3 mm) and people are typically reading or focusing on objects at an intermediate distance, the optical system defined by the eye and the IOL takes full advantage of the addition spherical aberration in the central portion of the IOL. Visual acuity in the near eye will decrease slightly, and depth of focus will increase, as compared to that associated with the EDF IOL described above. In low light conditions, where the pupil diameter is relatively large (e.g., greater than 3 mm) and distance and intermediate vision are typically more important, the outer region of the IOL will produce a significant amount of additional longitudinal spherical aberration and loss of visual acuity. In other words, although there are benefits associated with the additional spherical aberration, when combined with the normal physiological response of the pupil to low light conditions, there are also certain disadvantages. The IOLs described below are configured such that they accommodate the normal physiological response of the pupil to low light conditions to improve visual acuity in low light conditions despite the increase in spherical aberration.

An IOL that this otherwise identical to the IOLs described above with respect to, for example, FIGS. 6A and 6B, but for an increase in the amount of asphericity, is referred to herein as an EDF+IOL, while an IOL with both increased asphericity and the ability to accommodate the normal physiological response of the pupil to low light conditions is referred to herein as an EDF+A IOL.

Figure 11A:
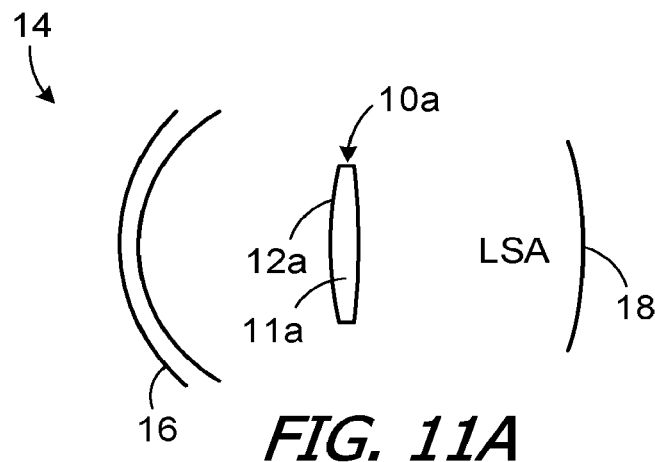
FIG. 11A is a schematic view of an optical system, including an IOL and an eye, in accordance with at least one embodiment of a present invention.

One example of an EDF+A IOL is identified by reference numeral 10a in FIG. 11A. The EDF+A IOL 10a has a lens body 11a and an aspheric lens surface 12a to provide the controlled spherical aberrations necessary to achieve the desired depth of focus and accommodate the normal physiological response of the pupil to low light conditions. Haptics (not shown) may also be provided. Although the aspheric surface 12a is the anterior surface in the illustrated embodiment and the posterior surface is spherical, the posterior surface may, alternatively or in addition, be aspheric. The EDF+A IOL 10a is shown as part of an optical system that also includes an eye 14 with a cornea 16 and retina 18. It should also be noted that the longitudinal spherical aberration values discussed below are measured from retina 18 towards the IOL in the region identified by "LSA" in FIG. 11A and, accordingly, the numeric values are negative. Thus, for example, −1.0 mm of LSA is more LSA than −0.5 mm of LSA. A process of designing such an IOL, and the resulting exemplary EDF+A IOLs, are discussed below. Toric IOLs and contact lenses are other examples of suitable optical devices that may be used to add higher order aberration to the eye in accordance with the present inventions.

The process for designing such an IOL is similar to that described above. For example, the exemplary IOL design specifications (Table 1), model eye (Table 2), and materials may be the same as those described above. The differences between the EDF IOLs described above, and the EDF+ and EDF+A IOLs, are discussed below.

The asphericity of the anterior surface of the optics was optimized using ZEMAX® optical design program in the model eye discussed above (Table 2). The merit function used for optimizing the lens design is the longitudinal aberration. Table 9 lists a pre-defined longitudinal spherical aberration for an exemplary EDF+A IOL for 20.0 D IOL power:

TABLE 9

Pre-Defined Longitudinal Spherical Aberration
(Variables for ZEMAX ® Merit Function)

| Zone | Target | Zone | Target | Zone | Target | Zone | Target |
|---|---|---|---|---|---|---|---|
| 0.00 | 0.000 | 0.26 | −0.119 | 0.52 | −0.431 | 0.78 | −0.802 |
| 0.02 | −0.001 | 0.28 | −0.137 | 0.54 | −0.459 | 0.80 | −0.827 |
| 0.04 | −0.003 | 0.30 | −0.156 | 0.56 | −0.488 | 0.82 | −0.851 |
| 0.06 | −0.007 | 0.32 | −0.177 | 0.58 | −0.518 | 0.84 | −0.874 |
| 0.08 | −0.012 | 0.34 | −0.199 | 0.60 | −0.547 | 0.86 | −0.896 |
| 0.10 | −0.018 | 0.36 | −0.221 | 0.62 | −0.576 | 0.88 | −0.916 |
| 0.12 | −0.026 | 0.38 | −0.245 | 0.64 | −0.606 | 0.90 | −0.935 |
| 0.14 | −0.035 | 0.40 | −0.269 | 0.66 | −0.635 | 0.92 | −0.952 |
| 0.16 | −0.046 | 0.42 | −0.294 | 0.68 | −0.664 | 0.94 | −0.967 |
| 0.18 | −0.058 | 0.44 | −0.320 | 0.70 | −0.693 | 0.96 | −0.980 |
| 0.20 | −0.071 | 0.46 | −0.347 | 0.72 | −0.721 | 0.98 | −0.991 |
| 0.22 | −0.086 | 0.48 | −0.374 | 0.74 | −0.749 | 1.00 | −1.000 |
| 0.24 | −0.102 | 0.50 | −0.402 | 0.76 | −0.776 | | |

The longitudinal spherical aberration of IOL power other than 20.0 D may be calculated by the equations discussed above. The radii design and shape factor, which were derived in the manner described above with reference to Table 4, are shown in Table 10 for the lens power range of 10.0 to 30.0 D with 0.5 D increments.

TABLE 10

Lens Radii, Shape Factors, and Thicknesses

| IOL Labeled Power (D) | Ant. Apex (mm) | Post. Radius (mm) | Shape Factor | Center Thickness (mm) | Edge Thickness (mm) |
|---|---|---|---|---|---|
| 10.0 | 35.00 | −36.9884 | −0.0276 | 0.5600 | 0.2085 |
| 10.5 | 35.00 | −33.5362 | 0.0214 | 0.5600 | 0.1959 |
| 11.0 | 35.00 | −30.6733 | 0.0659 | 0.5600 | 0.1833 |
| 11.5 | 35.00 | −28.2608 | 0.1065 | 0.5600 | 0.1707 |
| 12.0 | 35.00 | −26.2001 | 0.1438 | 0.5600 | 0.1580 |
| 12.5 | 35.00 | −24.4195 | 0.1781 | 0.5600 | 0.1454 |
| 13.0 | 26.90 | −28.4689 | −0.0283 | 0.5718 | 0.1800 |
| 13.5 | 26.90 | −26.3768 | 0.0098 | 0.5844 | 0.1800 |
| 14.0 | 26.90 | −24.5709 | 0.0453 | 0.5971 | 0.1800 |
| 14.5 | 26.90 | −22.9963 | 0.0782 | 0.6098 | 0.1800 |
| 15.0 | 26.90 | −21.6112 | 0.1090 | 0.6225 | 0.1800 |
| 15.5 | 22.30 | −24.1583 | −0.0400 | 0.6259 | 0.1800 |
| 16.0 | 22.30 | −22.6332 | −0.0074 | 0.6386 | 0.1800 |
| 16.5 | 22.30 | −21.2891 | 0.0232 | 0.6513 | 0.1800 |
| 17.0 | 22.30 | −20.0955 | 0.0520 | 0.6641 | 0.1800 |
| 17.5 | 22.30 | −19.0285 | 0.0792 | 0.6769 | 0.1800 |
| 18.0 | 19.10 | −20.9064 | −0.0452 | 0.6839 | 0.1800 |
| 18.5 | 19.10 | −19.7530 | −0.0168 | 0.6967 | 0.1800 |
| 19.0 | 19.10 | −18.7201 | 0.0100 | 0.7095 | 0.1800 |
| 19.5 | 19.10 | −17.7898 | 0.0355 | 0.7223 | 0.1800 |
| 20.0 | 19.10 | −16.9474 | 0.0597 | 0.7352 | 0.1800 |

TABLE 10-continued

Lens Radii, Shape Factors, and Thicknesses

| IOL Labeled Power (D) | Ant. Apex (mm) | Post. Radius (mm) | Shape Factor | Center Thickness (mm) | Edge Thickness (mm) |
|---|---|---|---|---|---|
| 20.5 | 16.60 | −18.5470 | −0.0554 | 0.7434 | 0.1800 |
| 21.0 | 16.60 | −17.6324 | −0.0302 | 0.7563 | 0.1800 |
| 21.5 | 16.60 | −16.8035 | −0.0061 | 0.7692 | 0.1800 |
| 22.0 | 16.60 | −16.0489 | 0.0169 | 0.7821 | 0.1800 |
| 22.5 | 16.60 | −15.3591 | 0.0388 | 0.7950 | 0.1800 |
| 23.0 | 14.60 | −16.7632 | −0.0690 | 0.8038 | 0.1800 |
| 23.5 | 14.60 | −16.0112 | −0.0461 | 0.8167 | 0.1800 |
| 24.0 | 14.60 | −15.3237 | −0.0242 | 0.8297 | 0.1800 |
| 24.5 | 14.60 | −14.6926 | −0.0032 | 0.8427 | 0.1800 |
| 25.0 | 14.60 | −14.1114 | 0.0170 | 0.8557 | 0.1800 |
| 25.5 | 13.10 | −15.1919 | −0.0739 | 0.8642 | 0.1800 |
| 26.0 | 13.10 | −14.5706 | −0.0531 | 0.8773 | 0.1800 |
| 26.5 | 13.10 | −13.9980 | −0.0331 | 0.8903 | 0.1800 |
| 27.0 | 13.10 | −13.4685 | −0.0139 | 0.9034 | 0.1800 |
| 27.5 | 13.10 | −12.9775 | 0.0047 | 0.9166 | 0.1800 |
| 28.0 | 11.80 | −13.9954 | −0.0851 | 0.9253 | 0.1800 |
| 28.5 | 11.80 | −13.4653 | −0.0659 | 0.9384 | 0.1800 |
| 29.0 | 11.80 | −12.9738 | −0.0474 | 0.9516 | 0.1800 |
| 29.5 | 11.80 | −12.5168 | −0.0295 | 0.9648 | 0.1800 |
| 30.0 | 11.80 | −12.0907 | −0.0122 | 0.9780 | 0.1800 |

The aspheric profile design ended up as a paraboloid with higher even order aspheric coefficients. The sag value of the even asphere surface is described by $z(r)$ equation above. The conic constant and higher order coefficients, for each band, are presented in Table 11.

TABLE 11

Exemplary Aspheric Coefficients for Each Band

| Mid-power in each band (D) | Even Asphere Coefficients | | |
|---|---|---|---|
| | Conic | $4^{th}$ order | $6^{th}$ order |
| 11.5 | 139.93054682 | 1.256208775e−003 | −1.652486759e−004 |
| 14.0 | 70.87022083 | 9.723253415e−004 | −1.342397470e−004 |
| 16.5 | 42.81316494 | 9.014026394e−004 | −1.254970439e−004 |
| 19.0 | 27.63623309 | 8.440403842e−004 | −1.185516133e−004 |
| 21.5 | 18.25663385 | 7.986651912e−004 | −1.130653821e−004 |
| 24.0 | 12.26910860 | 7.643229813e−004 | −1.089419999e−004 |
| 26.5 | 8.53594692 | 7.403617599e−004 | −1.061231959e−004 |
| 29.0 | 5.90947180 | 7.247535765e−004 | −1.044059419e−004 |

Figure 11B:
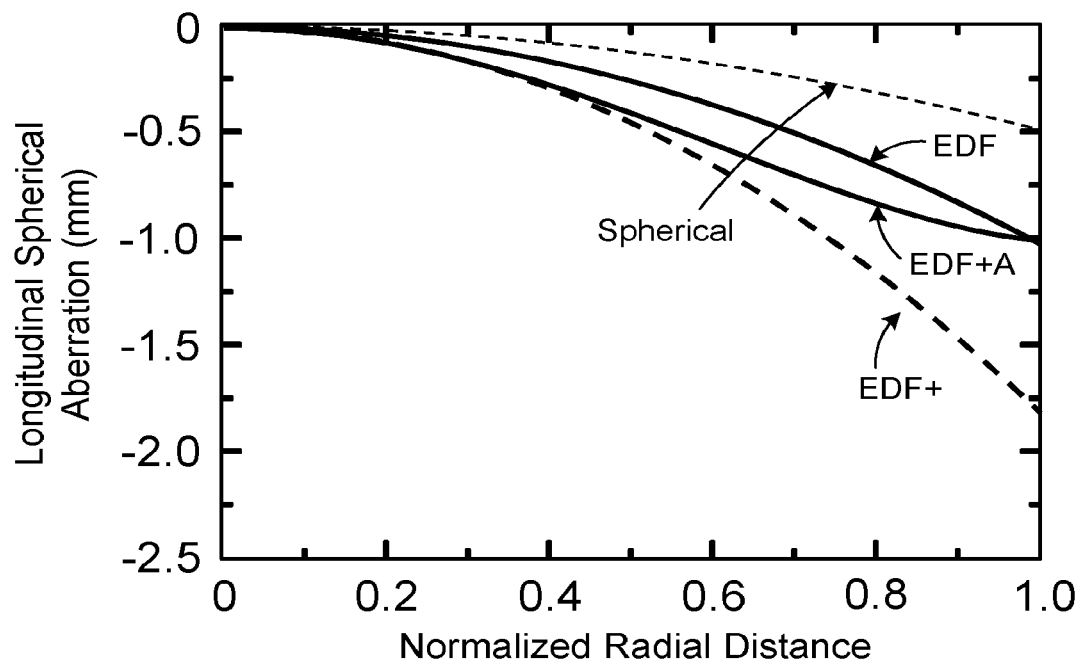
FIG. 11B is a graph showing longitudinal spherical aberration as a function of normalized radial distance for optical systems including IOLs in accordance with embodiments of the present inventions.

Turning to the performance of the EDF+A IOL described above, FIG. 11B illustrates the longitudinal spherical aberration in an optical system as a function of normalized radial distance (NRD), i.e. the normalized distance of an individual ray trace from the optical axis, for the EDF IOL described above (i.e., Tables 1-7), the EDF+A IOL described above (i.e., Tables 9-11), and an EDF+IOL (i.e., the EDF IOL with additional asphericity). An optical system with a conventional spherical IOL is also depicted in FIG. 11B for purpose of comparison. The NRD number increases with pupil diameter and, accordingly, the numbers closer to 0 are indicative of bright light conditions and the influence of the central portion of the IOL, and the numbers closer to 1.0 are indicative of low light conditions and the contribution across the entire diameter of the IOL. For spherical IOLs, EDF IOLs, and EDF+IOLs, the magnitude of the LSA is relatively low at the low end of the NRD scale (e.g., 0.3), and the LSA difference between the three IOLs is relatively low. The magnitude of slope of the LSA/NRD curve (or "profile"), i.e., the magnitude of the slope of the tangent at points along the curve, continuously increases from 0 to 1.0 NRD for all three IOLs. Note again that, for example, −1.0 LSA is more LSA than −0.5 LSA. The magnitude of the slope of the LSA/NRD curve for the EDF+IOL increases more rapidly than that of the spherical and EDF IOLs. This causes the curves (and the associated LSA values) to diverge significantly at the higher end of the NRD scale. As such, while the additional asphericity in the EDF+IOL does not result in a significant increase in LSA at the lower ("bright light") end of the NRD scale, as compared the EDF IOL, the additional asphericity in the EDF+IOL does add a significant amount of LSA at the higher ("low light") end of the NRD scale, as compared to the EDF IOL.

Like the EDF+IOL, the magnitude of the LSA for the EDF+A IOL is relatively low at the low end of the NRD scale, and the LSA difference between the EDF IOL and the EDF+A IOL is also relatively low. The magnitude of the slope of the LSA/NRD curve for the EDF+A IOL also increases more rapidly than that of the EDF IOL. In contrast to the EDF+IOL, however, the magnitude of the slope of the LSA/NRD curve does not continuously increase from 0 to 1.0 NRD. Rather, there is an inflection point (e.g., a point between 0.4 and 0.8 NRD) at which the magnitude of the slope of the LSA/NRD curve begins to decrease with NRD. The curves for the EDF and EDF+IOLs diverge at the higher end of the NRD scale, while the curves for the EDF and EDF+A IOLs converge (and in the exemplary embodiment, but not all embodiments, meet) at the higher end of the NRD scale, as illustrated in FIG. 11B. Thus, although the additional asphericity in the EDF+A IOL does add some LSA at the higher ("low light") end of the NRD scale, as compared to the EDF IOL, the increase is far less than that associated with the EDF+IOL.

Figure 12A:
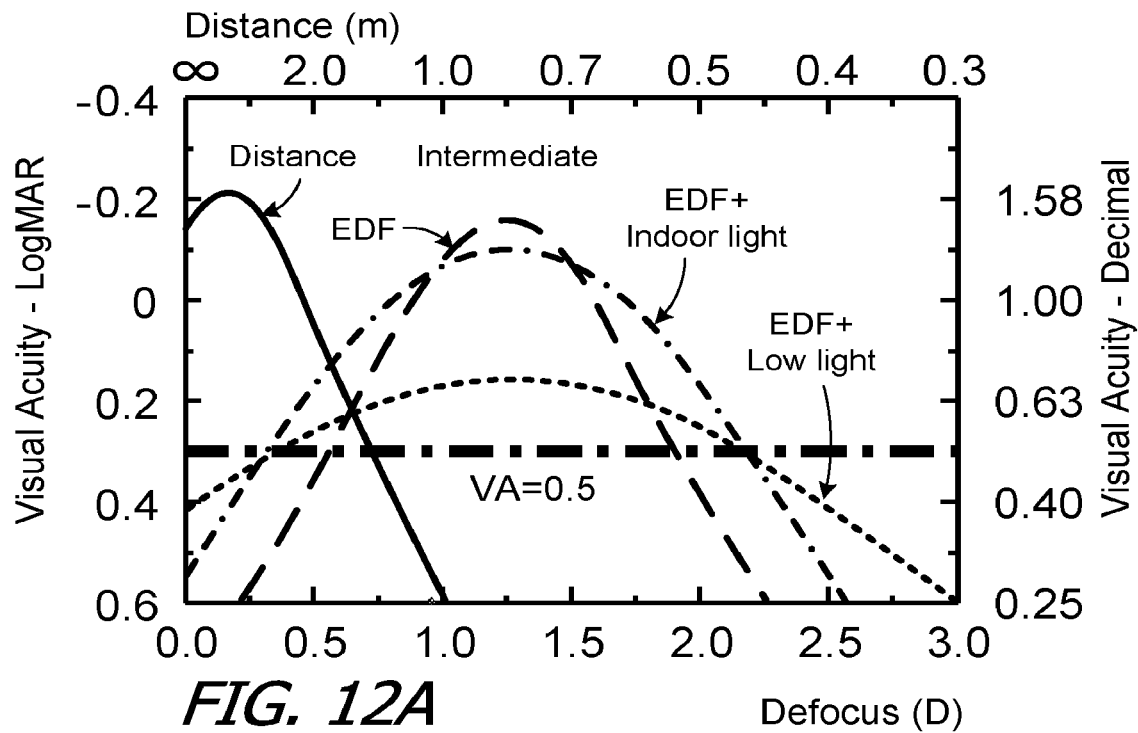
FIG. 12A is a graph showing visual acuity as a function of defocus in each eye after another pseudophakic monovision procedure in which the intermediate eye includes an aspheric IOL which adds more spherical aberration to the eye than that illustrated in FIG. 6A.
Figure 12B:
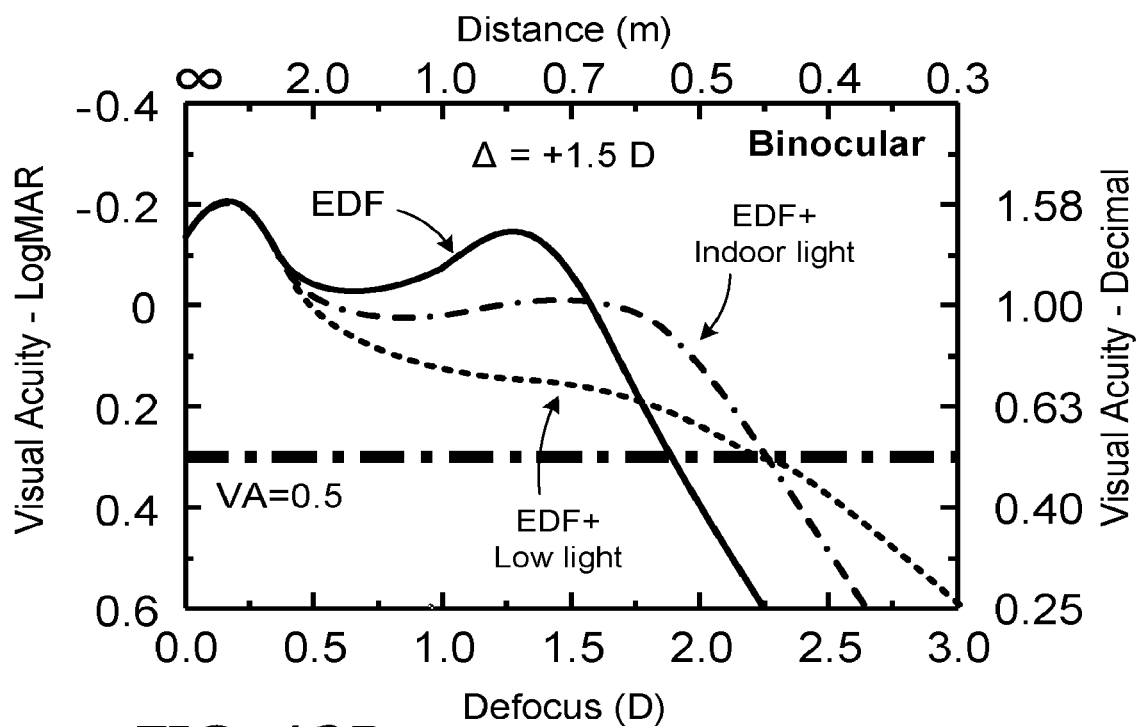
FIG. 12B is a graph showing binocular visual acuity as a function of defocus after the pseudophakic monovision procedure illustrated in FIG. 12A.

The advantages of an EDF+A IOL, as compared to EDF and EDF+IOLs, are illustrated in FIGS. 12A-13B. FIGS. 12A and 12B illustrate the use of an EDF+IOL in a modest monovision procedure similar to that illustrated in FIGS. 6A and 6B. The procedure involves inserting an aspheric IOL that eliminates (or at least substantially eliminates) spherical aberration into distance eye and inserting an IOL into the intermediate eye that may be about 1.0 to 1.5 D greater than the IOL for the distance eye (Δ=+1.5 D in the illustrated example). Here, however, the IOL that is inserted into the intermediate eye is an EDF+IOL that adds more spherical aberration to the eye than the EDF IOL. Referring to FIG. 12A, as compared to the intermediate eye with an EDF IOL in indoor/reading light conditions, the visual acuity of the intermediate eye with the EDF+IOL will be slightly less, but the depth of focus will be greater. In low light conditions, however, the visual acuity of the intermediate eye with the EDF+IOL will be significantly less. Thus, as is illustrated in FIG. 12B, the additional asphericity of the EDF+IOL in the intermediate eye results in additional depth of focus and better near vision in indoor light, but there is a significant loss of intermediate and near visual acuity in low light conditions.

Figure 13A:
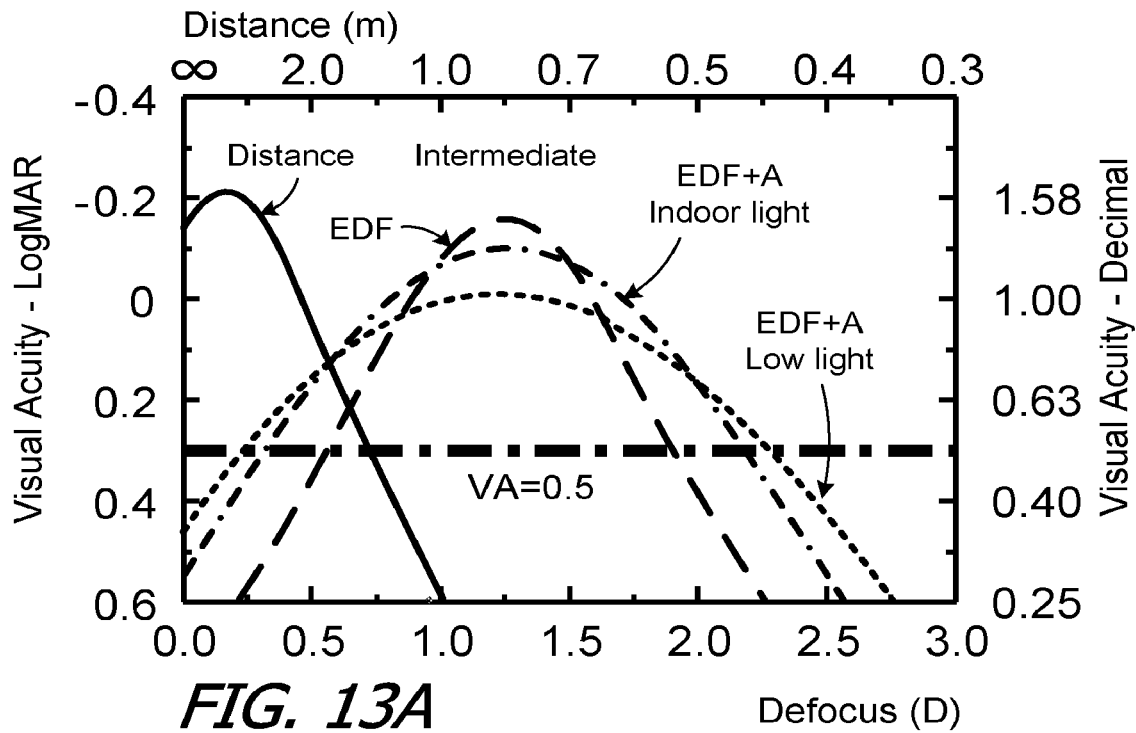
FIG. 13A is a graph showing visual acuity as a function of defocus in each eye after another pseudophakic monovision procedure, in accordance with a present invention, in which the intermediate eye includes the aspheric IOL which adds spherical aberration to the eye in a manner different than that illustrated in FIG. 12A.
Figure 13B:
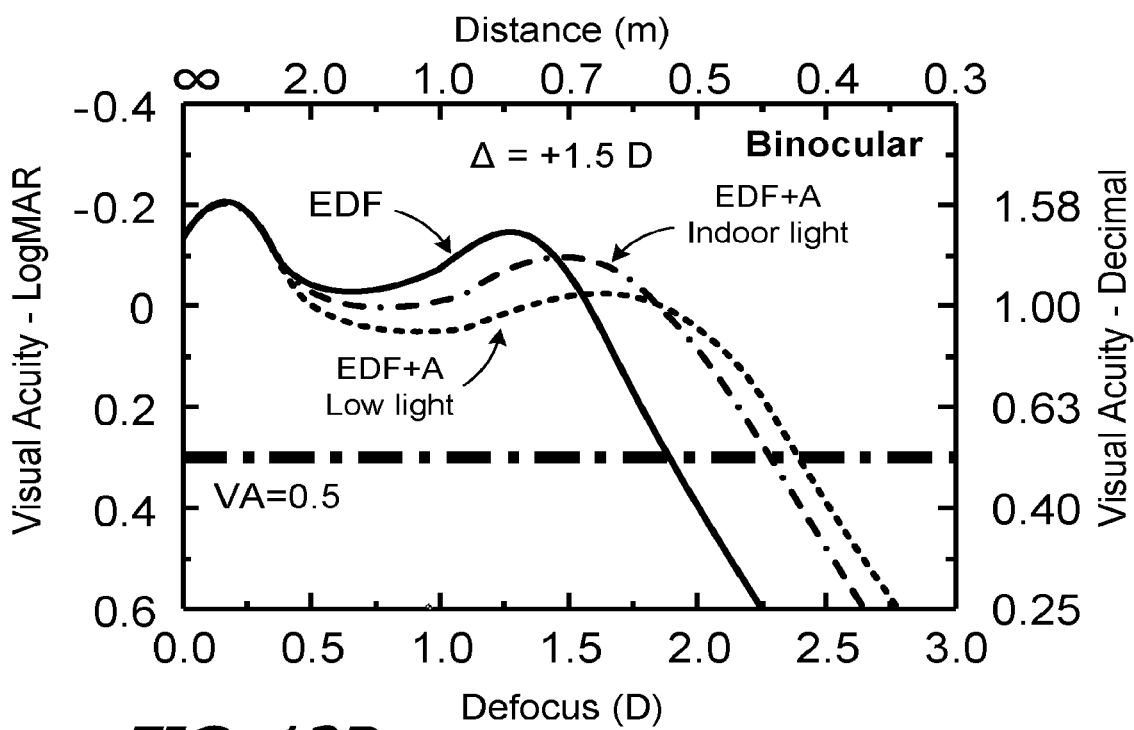
FIG. 13B is a graph showing binocular visual acuity as a function of defocus after the pseudophakic monovision procedure illustrated in FIG. 13A.

Turning to FIGS. 13A and 13B, which illustrate a modest monovision procedure with the EDF+A IOL described above, the ability to accommodate the physiological response of the pupil to low light conditions results better visual acuity in low light conditions than that associated with the EDF+IOL. The procedure also involves inserting an aspheric IOL that eliminates (or at least substantially eliminates) spherical aberration into the distance eye and inserting an IOL into the intermediate eye that may be about 1.0 to 1.5 D greater than the IOL for the distance eye (Δ=+1.5 D in the illustrated example). Here, however, the IOL that is inserted into the intermediate eye is an EDF+A IOL that adds the same spherical aberration to the eye as the EDF+IOL, but also has the ability to accommodate the increase in pupil size at low light conditions. Referring to FIG. 13A, as compared to the intermediate eye with an EDF IOL in indoor/reading light conditions, the visual acuity of the intermediate eye with the EDF+A IOL will be slightly less, but the depth of focus will be greater. There will also be a slightly greater loss visual acuity in the intermediate eye with the EDF+A IOL in low light conditions, but this loss will be significantly less than that associated with the EDF+IOL. Thus, as is illustrated in FIG. 13B, the additional asphericity of the EDF+A IOL in the intermediate eye results in additional depth of focus and better near vision in indoor light, without a significant loss of intermediate and near visual acuity in low light conditions.

Turning to the correction of chromatic aberration, best vision for the far vision eye can be achieved by correcting all corneal aberrations, including chromatic aberration due to the dispersiveness of the cornea. A pseudophakic IOL with a diffractive-refractive hybrid design can be used to correct chromatic aberration, in the manner described above, when EDF+ and EDF+A IOLs are employed in the near eye.

It should also be emphasized that the EDF+A IOL described above with reference to Tables 9-11 is merely one example of an IOL that both adds more spherical aberration than to the eye than a spherical IOL and reduces the amount longitudinal spherical aberration that will occur in low light conditions. To that end, another example is presented in Tables 12-14. The explanations above are applicable thereto. Here, the EDF++A IOL adds more spherical aberration to the eye than EDF+A IOL. Table 12 lists a pre-defined longitudinal spherical aberration for an exemplary EDF++A IOL for 20.0 D IOL power:

TABLE 12

Pre-Defined Longitudinal Spherical Aberration
(Variables for ZEMAX ® Merit Function)

| Zone | Target | Zone | Target | Zone | Target | Zone | Target |
|---|---|---|---|---|---|---|---|
| 0.00 | 0.000 | 0.26 | −0.149 | 0.52 | −0.524 | 0.78 | −0.915 |
| 0.02 | −0.001 | 0.28 | −0.171 | 0.54 | −0.558 | 0.80 | −0.937 |
| 0.04 | −0.004 | 0.30 | −0.195 | 0.56 | −0.591 | 0.82 | −0.956 |
| 0.06 | −0.008 | 0.32 | −0.221 | 0.58 | −0.624 | 0.84 | −0.973 |
| 0.08 | −0.015 | 0.34 | −0.247 | 0.60 | −0.657 | 0.86 | −0.988 |
| 0.10 | −0.023 | 0.36 | −0.275 | 0.62 | −0.689 | 0.88 | −0.999 |
| 0.12 | −0.033 | 0.38 | −0.303 | 0.64 | −0.721 | 0.90 | −1.008 |
| 0.14 | −0.044 | 0.40 | −0.333 | 0.66 | −0.752 | 0.92 | −1.014 |
| 0.16 | −0.058 | 0.42 | −0.363 | 0.68 | −0.782 | 0.94 | −1.016 |
| 0.18 | −0.073 | 0.44 | −0.395 | 0.70 | −0.812 | 0.96 | −1.015 |
| 0.20 | −0.089 | 0.46 | −0.426 | 0.72 | −0.840 | 0.98 | −1.009 |
| 0.22 | −0.108 | 0.48 | −0.459 | 0.74 | −0.867 | 1.00 | −1.000 |
| 0.24 | −0.127 | 0.50 | −0.491 | 0.76 | −0.892 | | |

The longitudinal spherical aberration of IOL power other than 20.0 D may be calculated by the equations discussed above. The radii design and shape factor, which were derived in the manner described above with reference to Table 4, are shown in Table 13 for the lens power range of 10.0 to 30.0 D with 0.5 D increments.

TABLE 13

Lens Radii, Shape Factors, and Thicknesses

| IOL Labeled Power (D) | Ant. Apex (mm) | Post. Radius (mm) | Shape Factor | Center Thickness (mm) | Edge Thickness (mm) |
|---|---|---|---|---|---|
| 10.0 | 35.00 | −36.9884 | −0.0276 | 0.5600 | 0.2271 |
| 10.5 | 35.00 | −33.5362 | 0.0214 | 0.5600 | 0.2145 |
| 11.0 | 35.00 | −30.6733 | 0.0659 | 0.5600 | 0.2019 |
| 11.5 | 35.00 | −28.2608 | 0.1065 | 0.5600 | 0.1893 |
| 12.0 | 35.00 | −26.2001 | 0.1438 | 0.5600 | 0.1767 |
| 12.5 | 35.00 | −24.4195 | 0.1781 | 0.5600 | 0.1640 |
| 13.0 | 26.90 | −28.4689 | −0.0283 | 0.6029 | 0.1800 |
| 13.5 | 26.90 | −26.3768 | 0.0098 | 0.6156 | 0.1800 |
| 14.0 | 26.90 | −24.5709 | 0.0453 | 0.6282 | 0.1800 |
| 14.5 | 26.90 | −22.9963 | 0.0782 | 0.6409 | 0.1800 |
| 15.0 | 26.90 | −21.6112 | 0.1090 | 0.6536 | 0.1800 |
| 15.5 | 22.30 | −24.1583 | −0.0400 | 0.6349 | 0.1800 |
| 16.0 | 22.30 | −22.6332 | −0.0074 | 0.6476 | 0.1800 |
| 16.5 | 22.30 | −21.2891 | 0.0232 | 0.6604 | 0.1800 |
| 17.0 | 22.30 | −20.0955 | 0.0520 | 0.6731 | 0.1800 |
| 17.5 | 22.30 | −19.0285 | 0.0792 | 0.6859 | 0.1800 |
| 18.0 | 19.10 | −20.9064 | −0.0452 | 0.6900 | 0.1800 |
| 18.5 | 19.10 | −19.7530 | −0.0168 | 0.7028 | 0.1800 |
| 19.0 | 19.10 | −18.7201 | 0.0100 | 0.7156 | 0.1800 |
| 19.5 | 19.10 | −17.7898 | 0.0355 | 0.7284 | 0.1800 |
| 20.0 | 19.10 | −16.9474 | 0.0597 | 0.7413 | 0.1800 |
| 20.5 | 16.60 | −18.5470 | −0.0554 | 0.7481 | 0.1800 |
| 21.0 | 16.60 | −17.6324 | −0.0302 | 0.7609 | 0.1800 |
| 21.5 | 16.60 | −16.8035 | −0.0061 | 0.7738 | 0.1800 |
| 22.0 | 16.60 | −16.0489 | 0.0169 | 0.7867 | 0.1800 |
| 22.5 | 16.60 | −15.3591 | 0.0388 | 0.7997 | 0.1800 |
| 23.0 | 14.60 | −16.7632 | −0.0690 | 0.8076 | 0.1800 |
| 23.5 | 14.60 | −16.0112 | −0.0461 | 0.8206 | 0.1800 |
| 24.0 | 14.60 | −15.3237 | −0.0242 | 0.8335 | 0.1800 |
| 24.5 | 14.60 | −14.6926 | −0.0032 | 0.8465 | 0.1800 |
| 25.0 | 14.60 | −14.1114 | 0.0170 | 0.8596 | 0.1800 |
| 25.5 | 13.10 | −15.1919 | −0.0739 | 0.8676 | 0.1800 |
| 26.0 | 13.10 | −14.5706 | −0.0531 | 0.8806 | 0.1800 |
| 26.5 | 13.10 | −13.9980 | −0.0331 | 0.8937 | 0.1800 |
| 27.0 | 13.10 | −13.4685 | −0.0139 | 0.9068 | 0.1800 |
| 27.5 | 13.10 | −12.9775 | 0.0047 | 0.9199 | 0.1800 |
| 28.0 | 11.80 | −13.9954 | −0.0851 | 0.9283 | 0.1800 |
| 28.5 | 11.80 | −13.4653 | −0.0659 | 0.9414 | 0.1800 |
| 29.0 | 11.80 | −12.9738 | −0.0474 | 0.9546 | 0.1800 |
| 29.5 | 11.80 | −12.5168 | −0.0295 | 0.9678 | 0.1800 |
| 30.0 | 11.80 | −12.0907 | −0.0122 | 0.9810 | 0.1800 |

The aspheric profile design ended up as a paraboloid with higher even order aspheric coefficients. The sag value of the even asphere surface is described by z(r) equation above. The conic constant and higher order coefficients, for each band, are presented in Table 14.

TABLE 14

Exemplary Aspheric Coefficients for Each Band

| Mid-power in each band (D) | Even Asphere Coefficients | | |
|---|---|---|---|
| | Conic | $4^{th}$ order | $6^{th}$ order |
| 11.5 | 146.93955781 | 1.852912938e−003 | −2.409593257e−004 |
| 14.0 | 78.16923295 | 1.480420843e−003 | −2.102013983e−004 |
| 16.5 | 47.12718748 | 1.434253240e−003 | −1.991468723e−004 |
| 19.0 | 30.87188687 | 1.367026522e−003 | −1.911554845e−004 |
| 21.5 | 20.72541713 | 1.310294262e−003 | −1.846236312e−004 |
| 24.0 | 14.17036609 | 1.265296813e−003 | −1.795289218e−004 |
| 26.5 | 10.05383814 | 1.231976419e−003 | −1.758315442e−004 |
| 29.0 | 7.11723500 | 1.208257548e−003 | −1.733635933e−004 |

Figure 14:
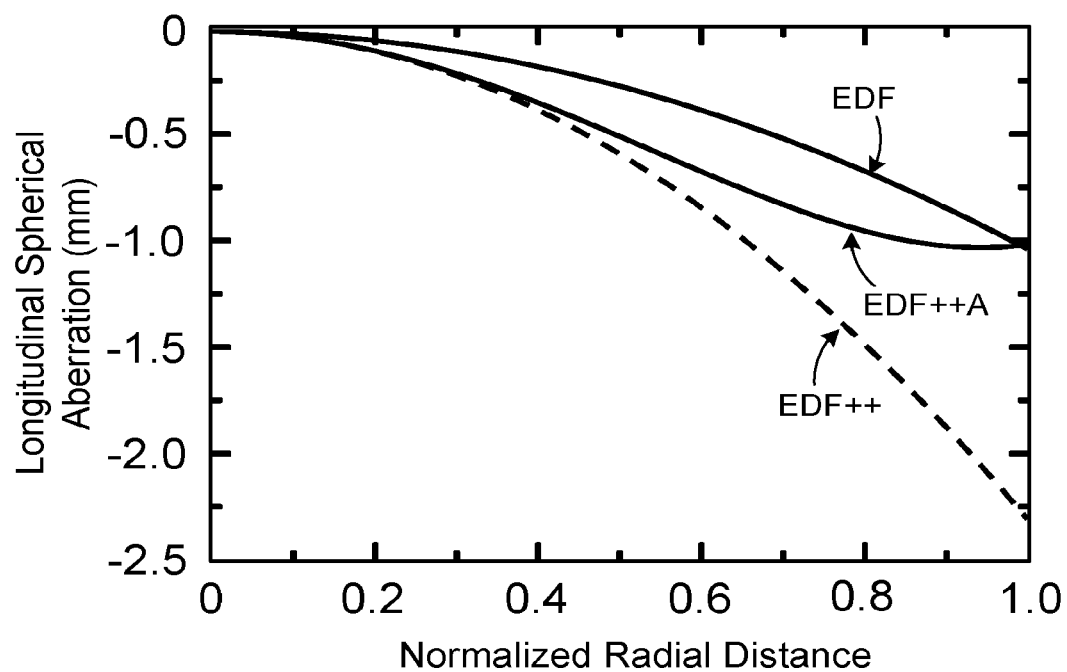
FIG. 14 is a graph showing longitudinal spherical aberration as a function of normalized radial distance for optical systems including IOLs in accordance with embodiments of the present inventions.

Turning to the performance of the EDF++A IOL outlined in Tables 12-14, FIG. 14 illustrates the longitudinal spherical aberration in an optical system as a function of normalized radial distance, i.e. the normalized distance of an individual ray trace from the optical axis, for the EDF IOL described above (i.e., Tables 1-7), the EDF++A IOL described above (i.e., Tables 12-14), and an EDF++IOL (i.e., the EDF IOL with the same amount of additional asphericity as the EDF++A IOL). For both EDF IOL and the EDF++IOL, the magnitude of the LSA is relatively low at the low end of the NRD scale, and the LSA difference between the two IOLs is relatively low. The magnitude of the slope of the LSA/NRD curve (or "profile") increases from 0 to 1.0 NRD for both IOLs, with the magnitude of the slope of the LSA/NRD curve for the EDF++IOL increasing more rapidly. This causes the curves (and the associated LSA values) to diverge significantly, and more so than the divergence associated with the EDF+IOL, at the higher end of the NRD scale. As such, while the additional asphericity in the EDF++IOL does not result in a significant increase in LSA at the lower ("bright light") end of the NRD scale, as compared the EDF IOL, the additional asphericity in the EDF++IOL does add a significant amount of LSA at the higher ("low light") end of the NRD scale, as compared to the EDF and the EDF+ IOLs.

The magnitude of the LSA for the EDF++A IOL is relatively low at the low end of the NRD scale, and the LSA difference between the EDF IOL and the EDF++A IOL is also relatively low. The magnitude of the slope of the LSA/NRD curve for the EDF++A IOL also increases more rapidly than that of the EDF IOL. In contrast to the EDF++ IOL, however, the magnitude of the slope of the LSA/NRD curve does not continuously increase from 0 to 1.0 NRD. Rather, there is an inflection point (e.g., a point between 0.4 and 0.8 NRD) at which the magnitude slope of the LSA/NRD curve begins to decrease with NRD. There is also a portion, near the 1.0 NRD, where the slope goes to zero and then changes sign. The curves for the EDF and EDF++IOLs diverge at the higher end of the NRD scale, while the curves for the EDF and EDF++A IOLs converge (and in the exemplary embodiment, but not all embodiments, meet) at the higher end of the NRD scale, as illustrated in FIG. 14. Thus, although the additional asphericity in the EDF++A IOL does add some LSA at the higher ("low light") end of the NRD scale, as compared to the EDF IOL, the increase is far less than that associated with the EDF++IOL.

Finally, the Table 15 below summarizes the wavefront spherical aberration (in μm) design model for the cornea, the model eye and the IOL at 4 mm and 6 mm entrance pupil for each of the designs at 20 D.

TABLE 15

Spherical Aberration Summary For Exemplary IOLs at 20 D

| Spherical Aberration (in μm) | | Aber. Free | Sphere | EDF | EDF+ | EDF+A | EDF++ | EDF++A |
|---|---|---|---|---|---|---|---|---|
| $Z_{4,6}^0$ | Corneal | 0.26 | 0.26 | 0.26 | 0.26 | 0.26 | 0.26 | 0.26 |
| 06 | Model Eye | 0.00 | 0.31 | 0.63 | 1.21 | 0.62 | 1.58 | 0.62 |
|  | Lens | −0.26 | +0.05 | +0.37 | +0.95 | +0.36 | +1.32 | +0.36 |
| $Z_{4,6}^0$ | Corneal | 0.05 | 0.05 | 0.05 | 0.05 | 0.05 | 0.05 | 0.05 |
| 04 | Model Eye | 0.00 | 0.07 | 0.11 | 0.21 | 0.16 | 0.27 | 0.20 |
|  | Lens | −0.05 | +0.02 | +0.06 | +0.16 | +0.11 | +0.22 | +0.15 |

The present inventions also include IOLs that result in LSA to NRD curves located between the curves for the EDF+A IOL (FIG. 11B) and EDF++A IOL (FIG. 14), as well as curves located above the EDF+A IOL curve and below the EDF++A IOL curve, so long as there is a reduction in the increase in magnitude of LSA at the upper end of the NRD scale.

The present inventions are not limited to the exemplary embodiments described above. Numerous other modifications and/or additions to the above-described preferred embodiments would be readily apparent to one skilled in the art. By way of example, but not limitation, IOLs which add negative spherical aberration that goes beyond correction to introduce spherical aberration may be employed. It is intended that the scope of the present inventions extends to all such modifications and/or additions.

What is claimed is:

1. A method comprising improving depth of focus in a first eye only by
    adding a higher order aberration (HOA) to the first eye by adding a monofocal optical device to the first eye, wherein the HOA is a longitudinal spherical aberration (LSA) and the LSA is less than or equal to 0 mm for all normalized radial distances.

2. The method of claim 1, wherein the method further comprises a step of correcting a spherical aberration in a second eye by inserting a monofocal aspheric IOL.

3. The method as claimed in claim 2, further comprising correcting a chromatic aberration in the second eye with the monofocal aspheric IOL.

4. The method as claimed in claim 1, wherein the HOA added to the first eye is selected from the group consisting of spherical, trefoil and coma.

5. The method as claimed in claim 1, wherein the monofocal optical device inserted into the first eye comprises a monofocal aspheric IOL that adds spherical aberration to the first eye.

6. The method as claimed in claim 5, wherein the optical device inserted into the first eye comprises a 20 D monofocal aspheric IOL that adds 0.4 μm of spherical aberration to the first eye at 6 mm entrance pupil and adds 0.1 μm of spherical aberration to the first eye at 4 mm entrance pupil.

7. The method as claimed in claim 1, wherein
    the monofocal optical device inserted into the first eye defines an optical center, an outer edge, a first region that extends from the optical center to a radius between the outer edge and the optical center, and a second region located radially outward of the first region; and
    the second region is configured to reduce a longitudinal HOA that will occur in low light conditions within an optical system defined by the monofocal optical device and the first eye.

8. The method as claimed in claim 7, wherein
    the monofocal optical device inserted into the first eye comprises a monofocal aspheric IOL;
    the HOA added to the first eye comprises a spherical aberration; and
    the longitudinal HOA comprises a longitudinal spherical aberration.

9. The method as claimed in claim 8, wherein the monofocal optical device inserted into the first eye is configured to create, within the optical system, a higher order aberration to normalized radial distance ratio (HOA-NRD ratio) profile that increases in slope as NRD increases within at least a portion of the first region and does not increase in slope as NRD increases within at least a portion of the second region.

10. The method as claimed in claim 9, wherein the HOA-NRD ratio profile increases in slope as NRD increases within the entire first region.

11. The method as claimed in claim 9, wherein the HOA-NRD ratio profile decreases in slope as NRD increases within at least a substantial majority of the second region.

12. The method as claimed in claim 9, wherein the first region and the second region are separated by an HOA-NRD profile inflection point.

13. The method as claimed in claim 12, wherein the inflection point is between an NRD of between 0.4 and 0.8.

* * * * *